(12) United States Patent
Kohgo et al.

(10) Patent No.: US 8,039,614 B2
(45) Date of Patent: Oct. 18, 2011

(54) 4'-C-SUBSTITUTED-2-HALOADENOSINE DERIVATIVE

(75) Inventors: Satoru Kohgo, Kashima-gun (JP); Hiroshi Ohrui, Sendai (JP); Eiichi Kodama, Kyoto (JP); Masao Matsuoka, Otsu (JP); Hiroaki Mitsuya, Kumamoto (JP)

(73) Assignee: Yamasa Corporation, Chiba (JP)

( * ) Notice: Subject to any disclaimer, the term of this patent is extended or adjusted under 35 U.S.C. 154(b) by 232 days.

(21) Appl. No.: 12/453,732

(22) Filed: May 20, 2009

(65) Prior Publication Data

US 2009/0234110 A1    Sep. 17, 2009

Related U.S. Application Data

(63) Continuation of application No. 11/984,527, filed on Nov. 19, 2007, now Pat. No. 7,625,877, which is a continuation of application No. 11/087,588, filed on Mar. 24, 2005, now Pat. No. 7,339,053.

(30) Foreign Application Priority Data

Mar. 24, 2004   (JP) ................. 2004-087198
Sep. 10, 2004   (JP) ................. 2004-263409

(51) Int. Cl.
*C07H 19/173*    (2006.01)
(52) U.S. Cl. .................. 536/27.11; 536/27.14
(58) Field of Classification Search ............. None
See application file for complete search history.

(56) References Cited

U.S. PATENT DOCUMENTS

| | | | |
|---|---|---|---|
| 5,192,749 | A | 3/1993 | O-Yang et al. |
| 7,339,053 | B2 * | 3/2008 | Kohgo et al. ........... 536/26.7 |
| 7,625,877 | B2 * | 12/2009 | Kohgo et al. ........... 514/46 |
| 2004/0167096 | A1 | 8/2004 | Cheng et al. |

FOREIGN PATENT DOCUMENTS

| | | |
|---|---|---|
| WO | 00/69876 | 11/2000 |
| WO | 00/69877 | 11/2000 |
| WO | 03/068796 | 8/2003 |
| WO | 2005/090349 | 9/2005 |

OTHER PUBLICATIONS

International Preliminary Report on Patentability issued Oct. 18, 2006 in the International (PCT) Application (PCT/JP2005/005374) of which U.S. Appl. No. 11/087,588 is the U.S. National Stage.
K. Kitano et al., "Synthesis of 4'-ethynyl-purine nucleosides possessing anti-HIV activity", Nucleic Acids Symposium Series, No. 44, pp. 105-106, Jan. 2000.
H. Ohrui et al., "Syntheses of 4'-C-Ethynyl-β-D-arabino- and 4'-C-Ethynyl-2'-deoxy-β-D-ribo-pentofuranosylpyrimidines and -purines and Evaluation of their Anti-HIV activity", J. Med. Chem., vol. 43, No. pp. 4516-4525, Nov. 2000.

H. Ohrui et al., "4'-C-Substituted-2'-Deoxynucleosides: A Family of Antiretroviral Agents which are Potent Against Drug-Resistant HIV Variants", Current Drug Targets Infectious Disorders, vol. 1, No. 1, pp. 1-10, May 2001.
E. Kodama et al., "4'-Ethynyl Nucleoside Analogs: Potent Inhibitors of Multidrug-Resistant Human Immunodeficiency Virus Variants In Vitro", Antimicrobial Agents and Chemotherapy, vol. 45, No. 5, pp. 1539-1546, May 2001.
S. Kohgo et al., "Synthesis of 4'-C-Ethynyl and 4'-C-Cyano Purine Nucleosides from Natural Nucleosides and Their Anti-HIV Activity", Nucleosides, Nucleotides & Nucleic Acids, vol. 22, Nos. 5-8, pp. 887-889, 2003.

(Continued)

*Primary Examiner* — Lawrence E Crane
(74) *Attorney, Agent, or Firm* — Wenderoth, Lind & Ponack, L.L.P.

(57) ABSTRACT

The present invention provides a method for producing a 4'-C-substituted-2-haloadenosine derivative represented by the following formula [I], [II], or [III]:

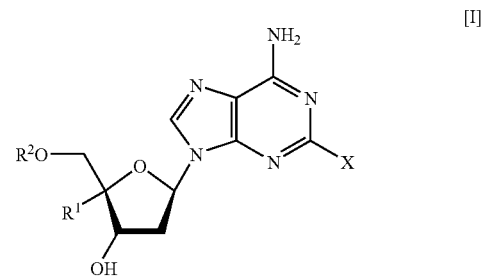

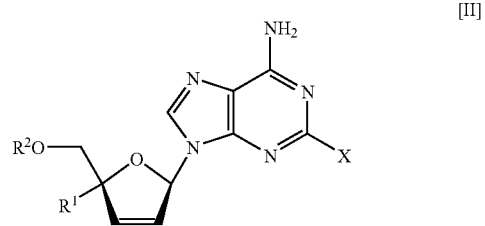

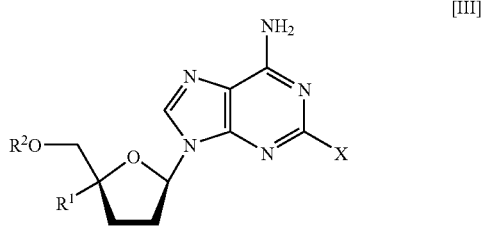

wherein X represents a halogen atom, $R^1$ represents an ethynyl group or a cyano group, and $R^2$ represents hydrogen or a phosphoryl group. The present invention also provides the derivative, and a pharmaceutical composition containing the derivative and a pharmaceutically acceptable carrier therefor. The derivative is useful as a medicine for the treatment of Acquired Immune Deficiency Syndrome (AIDS).

2 Claims, 3 Drawing Sheets

OTHER PUBLICATIONS

S. Shuto et al., "New Neplanocin Analogues. IV. 2-Fluoroneplanocin A: An Adenosine Deaminase-Resistant Equivalent of Neplanocin A[1]", Chem. Pharma. Bull., vol. 42, No. 8, pp. 1688-1690, 1994.

T. Obara et al., "New Neplanocin Analogues. 7. Synthesis and Antiviral Activity of 2-Halo Derivatives of Neplanocin A[1]", J. Med. Chem., vol. 39, No. 19, pp. 3847-3852, 1996.

K. Haraguchi et al., "Synthesis of a Highly Active New Anti-HIV Agent 2',3'-Didehydro-3'-deoxy-4'- ethynylthymidine", Bioorganic & Medicinal Chemistry Letters, vol. 13, No. 21, pp. 3775-3777, 2003.

H. Ohrui et al., "4'C-Ethynyl-2'-deoxy-2-fluoroadenosine, a nucleoside derivative with supreme activity against a wide spectrum of HIVs and low toxicity: Highlights of the role of 3'-OH for biological activity", 18th International Conference on Antiviral Research, Abstract: Preview Submission, Apr. 14-18, 2005.

S. Kohgo et al., "Synthesis of 4'-substituted nucleosides and their biological evaluation", Nucleic Acids Symposium Series, No. 42, pp. 127-128, 1999.

R. Yamaguchi et al., "Synthesis of 4'-C-Ethynyl-β-D-ribo-pentofuranosyl Pyrimidines", Biosci. Biotechnol. Biochem., vol. 63, No. 4, pp. 736-742, 1999.

D Salvatori et al., "Adenine and deazaadenine nucleoside and deoxynucleoside analogues: inhibition of viral replication of sheep MVV (in vitro model of HIV) and bovine BHV-1", Bioorganic and Medicinal Chemistry, vol. 10, pp. 2973-2980, 2002.

H. Ohrui et al., "4'C-Ethynyl-2'-deoxy-2-fluoroadenosine, a nucleoside derivative with supreme activity against a wide spectrum of HIVs and low toxicity: Highlights of the role of 3'-OH for biological activity", 18th International Conference on Antiviral Research, Apr. 14-18, 2005.

S. Kohgo et al., "Synthesis of 4'-C-Ethynyl-β-D-arabino -and 4'-C-Ethynyl-2'-deoxy-β-D-ribo-pentofuranosyl Pyrimidines, and Their Biological Evaluation", Biosci. Biotechnol. Biochem., vol. 63, No. 6, pp. 1146-1149, 1999.

H. Ohrui, "4'-C-Substituted-2'-Deoxy Nucleosides: Nucleosides Highly Active Against all kind of HIVs", XXIst European Colloquinum on Heterocyclic Chemistry, 2004.

S. Kohgo et al., "Synthesis of the L-Enantiomer of 4'-C-Ethynyl-2'-deoxycytidine", Biosci. Biotechnol. Biochem., vol. 65, No. 8, pp. 1879-1882, 2001.

K. Kitano et al., "Attempt to reduce cytotoxicity by snythesizing the L-enantiomer of 4'-C-ethynyl-2'-deoxypurine nucleosides as antiviral agents against HIV and HBV", Antiviral Chemistry & Chemotherapy, vol. 14, pp. 161-167, 2004.

H. Hayakawa et al., "Potential of 4'-C-substituted nucleosides for the treatment of HIV-1", Antiviral Chemistry & Chemotherapy, vol. 15, pp. 169-187, 2004.

S. Kohgo et al., "Design, Efficient Synthesis, and Anti-HIV Activity of 4'-C-Cyano- and 4'-C-Ethynyl-2'-deoxy Purine Nucleosides", Nucleosides, Nucleotides and Nucleic Acids, vol. 23, No .4, pp. 671-690, 2004.

M. Nomura et al., "Nucleosides and Nucleotides. 185. Synthesis and Biological Activities of 4'α-C-Branched-Chain Sugar Pyrimidine Nucleosides", J. Med. Chem., vol. 42, pp. 2901-2908, 1999.

M. Siddiqui et al., "A 4'-C-Ethynyl-2',3'-Dideoxynucleoside Analogue Highlights the Role of the 3'-OH in Anti-HIV Active 4'-C-Ethynyl-2'-deoxy Nucleosides", J. Med. Chem., vol. 47, pp. 5041-5048, 2004.

K. Haraguchi et al., "Synthesis and Anti-HIV activity of 4'-Cyano-2',3'-didehydro-3'-deoxythymidine", Nucleosides, Nucleotides & Nucleic Acids, vol. 23, No. 4, pp. 647-654, 2004.

G. E. Dutschman et al., "Novel 4'-Substituted Stavudine Analog with Improved Anti-Human Immunodeficiency Virus Activity and Decreased Cytotoxicity", Antimicrobial Agents and Chemotherapy, vol. 48, No. 5, pp. 1640-1646, May 2004.

X. Chen et al., "Synthesis of 3'-Fluoro-2',3'-dideoxy-2',3'-didehydro-4'-ethynyl-D-and -L-furanosyl Nucleosides", J. Org. Chem., vol. 69, pp. 6034-6041, 2004.

D. Summerer et al., "4'C-Ethynyl-thymidine acts as a chain terminator during DNA-synthesis catalyzed by HIV-1 reverse transcriptase", Bioorganic & Medicinal Chemistry Letters, vol. 15, pp. 869-871, 2005.

* cited by examiner

4'-C-SUBSTITUTED-2-HALOADENOSINE DERIVATIVE

This application is a continuation of Ser. No. 11/984,527, filed Nov. 19, 2007, now U.S. Pat. No. 7,625,877, which is a continuation of Ser. No. 11/087,588, filed Mar. 24, 2005, now U.S. Pat. No. 7,339,053.

BACKGROUND OF THE INVENTION

1. Field of the Invention

The present invention relates to 4'-C-substituted-2-haloadenosine derivatives and use thereof as a medicine, in particular a medicine which is useful for the treatment of acquired immunodeficiency syndrome (AIDS).

2. Background Art

The clinical setting for AIDS has been dramatically changed by a multi-drug combination therapy, which is sometimes called highly active antiretroviral therapy, or HAART. In HAART, nucleoside reverse transcriptase inhibitors (NRTIs) such as zidovudine (AZT), didanosine (ddI), zalcitabine (ddC), stavudine (d4T), and lamivudine (3TC), and protease inhibitors (PIs) are employed in combination.

Although HAART has drastically decreased the number of deaths caused by AIDS, there has emerged a multi-drug resistant HIV-1 (human immunodeficiency virus-1) mutant exhibiting cross-resistance to various drugs. For example, in the early 1990s patients infected with an HIV exhibiting resistance to both AZT and 3TC were very rare, whereas in 1995-1996 the percentage of AIDS patients infected with such an HIV became as high as 42%.

Ohrui, et al. have synthesized 2'-deoxy-4'-C-ethynyl nucleosides and assayed the anti-HIV activity thereof, and as a result, have found that a 2'-deoxy-4'-C-ethynyl nucleoside having a specific structure exhibits potent anti-HIV activity equal to or higher than that of AZT, and has effective antiviral activity against a multi-drug-resistant viral strain exhibiting resistance to various anti-HIV drugs such as AZT, ddI, ddC, d4T, and 3TC. (See, for example, Nucleic Acids Symp. Ser., January 2000, (44): 105-6; J. Med. Chem., November 2000, 43 (23): 4516-25; Curr. Drug Targets Infect. Disord, May 2001, 1 (1): 1-10; Antimicrob. Agents Chemother., May 2001, 45: 1539-1546; Nucleosides Nucleotides Nucleic Acids, May 2003, 22 (5-8): 887-9; WO 00/69876; WO 00/69877; and WO 03/68796).

The present inventors have evaluated in vitro toxicity of 4'-C-ethynyl purine nucleoside derivatives and 4'-C-cyano purine nucleoside derivatives, which, among a variety of 4'-C-substituted nucleosides, exhibit particularly potent anti-HIV activity. As a result, the present inventors have found that: (1) 2,6-diaminopurine derivatives and guanine derivatives, which exhibit the most potent anti-HIV activity, exhibit toxicity in vitro and in vivo; and (2) adenine derivatives, which exhibit less toxicity, are readily converted into hypoxanthine derivatives in blood by adenosine deaminase, thereby weakening the anti-HIV activity of the derivatives.

In order to attain further enhancement of selectivity index; i.e., (concentration at which cytotoxicity is obtained)/(concentration at which anti-HIV activity is obtained) and to provide resistance to inactivation by adenosine deaminase, the present inventors have synthesized a variety of derivatives through chemical modification of 4'-C-substituted-2'-deoxyadenosine (a lead compound), which, among various 4'-C-substituted purine nucleosides, exhibits potent anti-HIV activity and less toxicity.

As has been known, when a halogen atom, which exhibits electron attraction, is introduced to the 2-position of the base moiety of an adenosine derivative, the resultant derivative exhibits a certain level of resistance to inactivation by adenosine deaminase (Chem. Pharm. Bull., 42 (1994), p 1688; J. Med. Chem., 39 (1996), p 3847). However, whether or not selectivity index can be improved through introduction of a halogen atom has remained unknown.

Only one literature discloses that introduction of an ethynyl group to the 4'-position of d4T (stavudine: 2',3'-didehydro-3'-deoxythymidine) enhances the selectivity index of d4T (Bioorg. Med. Chem. Lett., November 2003, 13 (21): 3775-7). However, effects similar to those of d4T are not expected to be obtained in an adenosine derivative, which is a purine nucleoside, whose basic skeleton differs considerably from that of d4T, and therefore, this literature does not provide useful information for the present inventors' purposes.

SUMMARY OF THE INVENTION

The present inventors have performed studies on the anti-HIV activity, etc. of the newly synthesized derivatives, and have found that 2'-deoxy-4'-C-ethynyl-2-fluoroadenosine—which is obtained by introducing a fluorine atom to the 2-position of the base moiety of 2'-deoxy-4'-C-ethynyladenosine (i.e., lead compound)—exhibits resistance to inactivation by adenosine deaminase, has potent antiviral activity against a multi-drug-resistant virus strain exhibiting resistance to various anti-HIV drugs such as AZT, ddI, ddC, d4T, and 3TC, and exhibits enhanced anti-HIV activity and considerably lowered cytotoxicity.

On the basis of this finding, the present inventors have synthesized a variety of 4'-C-substituted-2-haloadenosine derivatives, each being formed of 2-haloadenine (base moiety) and a sugar moiety having an ethynyl or cyano group at the 4-position, and have assayed biological activities of the thus-synthesized derivatives. The present invention has been accomplished on the basis of the results of the assay.

Accordingly, the present invention provides a 4'-C-substituted-2-haloadenosine derivative represented by the following formula [I], [II], or [III]:

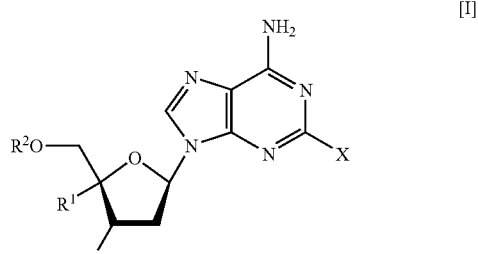

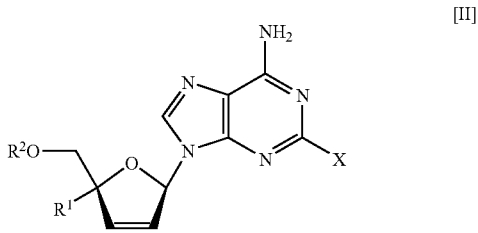

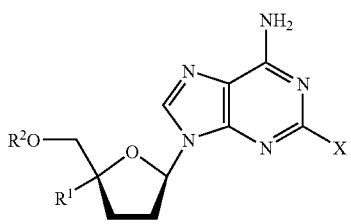

[III]

(wherein X represents a halogen atom, $R^1$ represents an ethynyl group or a cyano group, and $R^2$ represents hydrogen, a phosphate residue, or a phosphate derivative residue).

The present invention also provides a pharmaceutical composition containing the 4'-C-substituted-2-haloadenosine derivative and a pharmaceutically acceptable carrier therefor.

The present invention also provides a method of treating AIDS, comprising administering, to a human or an animal, the 4'-C-substituted-2-haloadenosine derivative or a pharmaceutical composition containing the derivative.

As shown in the Test Examples provided hereinbelow, the compounds of the present invention (e.g., 2'-deoxy-4'-C-ethynyl-2-fluoroadenosine) exhibit resistance to inactivation by adenosine deaminase, have potent antiviral activity against a multi-drug-resistant virus strain exhibiting resistance to various anti-HIV drugs such as AZT, ddI, ddC, d4T, and 3TC, exhibit unexpectedly enhanced anti-HIV activity; specifically, anti-HIV activity higher by a factor of 144 than that of 2'-deoxy-4'-C-ethynyladenosine (i.e., lead compound), and exhibit considerably lowered cytotoxicity. Therefore, surprisingly, the compounds of the present invention exhibit a selectivity index of 110,000, which is considerably higher than that of 2'-deoxy-4'-C-ethynyladenosine (EdAdo) (i.e., 1,630).

As described above, the compounds of the present invention exhibit excellent anti-HIV activity, particularly against a multi-drug-resistant HIV strain having resistance to various anti-HIV drugs such as AZT, DDI, DDC, D4T, and 3TC, exhibit less cytotoxicity, and exhibit resistance to inactivation by adenosine deaminase. Therefore, the compounds of the present invention are envisaged for development for producing pharmaceuticals, particularly drugs for treating AIDS.

BRIEF DESCRIPTION OF THE DRAWINGS

In FIG. 4, Graph A shows the results obtained from oral administration, and graph B shows the results obtained from intravenous injection. In both graphs, white circles show the results from placebo administration, and triangles and squares correspond to a dose of 30 mg/kg and 100 mg/kg, respectively.

Figure 1:
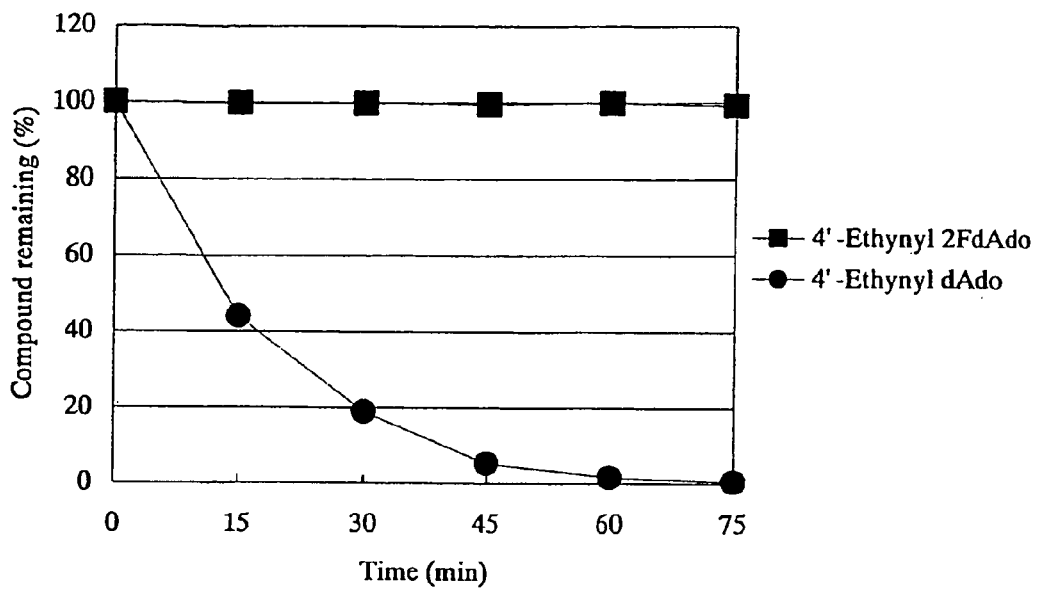
FIG. 1 shows stability of compounds against deamination reaction induced by adenosine deaminase. The black squares show the results obtained from 2'-deoxy-4'-C-ethynyl-2-fluoroadenosine (a compound of the present invention), whereas the black circles show the results obtained from 2'-deoxy-4'-C-ethynyladenosine (a known compound)

DETAILED DESCRIPTION OF PREFERRED EMBODIMENTS (1) Compounds

The compounds of the present invention are represented by formulas [I], [II], and [III]. Examples of the phosphate residue represented by $R^2$ in these formulas include a monophosphate residue, a diphosphate residue, a triphosphate residue, and a phosphonate; and examples of the phosphate derivative residue include phosphate polyesters (e.g., a phosphate diester and a phosphate triester), phosphate amidates (e.g., a phosphate monoamidate and a phosphate diamidate), phosphorothioate, phosphoroselenoate, and phosphoroboranoate. Examples of halogen atoms represented by X include bromine, iodine, fluorine, and chlorine.

Of these compounds, preferred ones are those that satisfy one or more of the following requirements: (a) $R^2$ is hydrogen or phosphonate; (b) X is fluorine or chlorine; and (c) $R^1$ is an ethynyl group. Specific examples of preferred compounds are given below:
<Compounds Represented by Formula [I]>
2'-deoxy-4'-C-ethynyl-2-fluoroadenosine, 4'-C-cyano-2'-deoxy-2-fluoroadenosine, 2-chloro-2'-deoxy-4'-C-ethynyladenosine, and 2'-deoxy-4'-C-ethynyl-2-fluoroadenosine 5'-H-phosphonate;
<Compounds Represented by Formula [II]>
2',3'-didehydro-2',3'-dideoxy-4'-C-ethynyl-2-fluoroadenosine, 2',3'-didehydro-2',3'-dideoxy-4'-C-cyano-2-fluoroadenosine, 2',3'-didehydro-2',3'-dideoxy-4'-C-ethynyl-2-chloroadenosine, and 2',3'-didehydro-2',3'-dideoxy-4'-C-ethynyl-2-fluoroadenosine 5'-H-phosphonate; and
<Compounds Represented by Formula [III]>
2',3'-dideoxy-4'-C-ethynyl-2-fluoroadenosine, 2',3'-dideoxy-4'-C-cyano-2-fluoroadenosine, 2',3'-dideoxy-4'-C-ethynyl-2-chloroadenosine, and 2',3'-dideoxy-4'-C-ethynyl-2-fluoroadenosine 5'-H-phosphonate.

The compounds of the present invention may be salts, hydrates, or solvates. When $R^2$ is hydrogen, examples of salts include acid-adducts such as hydrochlorides and sulfates; and when $R^2$ is a phosphate-residue, examples of salts include alkali metal salts such as sodium salts, potassium salts, and lithium salts; alkaline earth metal salts such as calcium salts; and ammonium salts, and any of those salts may be used so long as they are pharmaceutically acceptable.

Examples of hydrates or solvates include adducts formed by combining one molecule of the compound of the present invention or a salt thereof and 0.1-3.0 molecules of water or a solvent. In addition, the compounds of the present invention encompass a variety of isomers thereof such as tautomers.

(2) Production Method

The compounds [I] of the present invention can be produced through the below-described steps.

First Step:

In the first step, hydroxyl groups at the 3'- and 5'-positions of a compound represented by formula [IV] are protected, to thereby yield a compound represented by formula [V]:

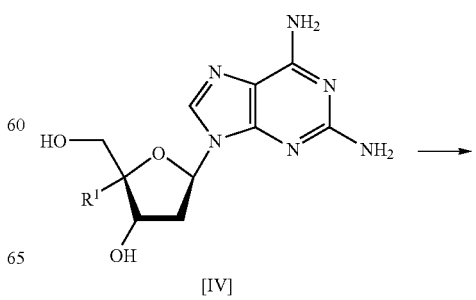

[IV]

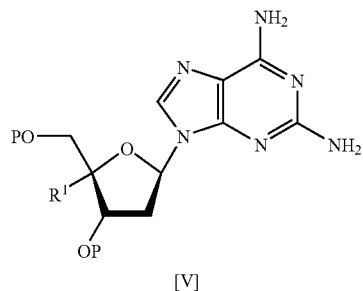

[V]

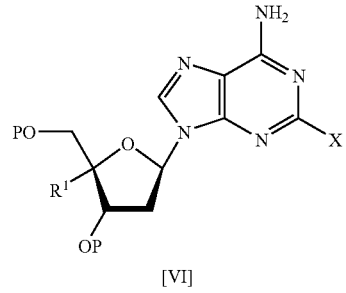

[VI]

(wherein P represents a protective group, and $R^1$ represents an ethynyl group or a cyano group).

The compound [IV] (i.e., starting material) is a known compound; specifically, a compound in which $R^1$ is an ethynyl group (J. Med. Chem., 43, 4516-4525 (2000)), or a compound in which $R^1$ is a cyano group (WO 03/68796).

The protective groups represented by P, which protect the hydroxyl groups at the 3'- and 5'-positions, may be those groups which are generally employed for protecting a hydroxyl group. Examples of types of the protective groups include an ether type, an acyl type, a silyl type, and an acetal type. Specific examples of the protective groups which may be employed include ether-type protective groups such as methyl ether, tert-butyl ether, benzyl ether, methoxybenzyl ether, and trityl ether; acyl-type protective groups such as acetyl, benzoyl, and pivaloyl; silyl-type protective groups such as t-butyldimethylsilyl, t-butyldiphenylsilyl, trimethylsilyl, and triethylsilyl; and acetal-type protective groups such as isopropylidene, ethylidene, methylidene, benzylidene, tetrahydropyranyl, and methoxymethyl.

Introduction of a protecting group is performed by conventional methods. For examples, in organic solvent such as pyridine, acetonitrile or dimethylformamide, compound [IV] is allowed to react with a protecting agent (alkyl halide, acid halide, acid anhydride or alkylsilyl halide) in the presence of a base such as metal alkoxide, triethylamine, 4-dimethylaminopyridine or imidazole, at −10 to 100° C.

Second Step:

In the second step, the amino group at the 2-position of the compound [V] is converted into a halogen atom, to thereby yield a compound represented by formula [VI]:

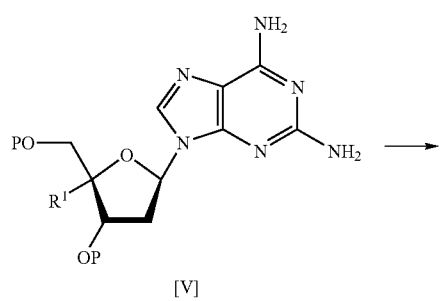

[V]

(wherein P represents a protective group, X represents a halogen atom, and $R^1$ represents an ethynyl group or a cyano group).

The compound [VI] can be synthesized through the following procedure: after the amino group at the 2-position of the compound [V] is treated with a nitrite derivative, halogen atom is introduced at the 2-position of the base moiety by use of a halogen reagent; or the amino groups at the 2- and 6-positions are treated under the same conditions, thereby forming a 2,6-dihalopurine derivative, and the halogen atom at the 6-position of the base moiety is converted into an amino group through treatment with ammonia.

Examples of reagents for substituting the amino group at the 2-position of the compound [V] by fluorine include sodium nitrite in tetrafluoroboric acid; and a nitrous acid ester (e.g., t-butyl nitrite) in hydrogen fluoride-pyridine.

Reaction conditions vary depending on the reagent employed. For example, when t-butyl nitrite is employed in hydrogen fluoride-pyridine, t-butyl nitrite (1 to 3 mol) is added to the compound [V] in hydrogen fluoride-pyridine serving as a solvent, and the resultant mixture is allowed to react at −50° C. to room temperature for about 15 minutes to about five hours. When the compound [V] is formed into a 2,6-difluoropurine derivative, the resultant derivative is treated with aqueous ammonia in an organic solvent such as dioxane or methanol.

Examples of reagents for substituting the amino group at the 2-position of the compound [V] by chlorine include a combination of antimony trichloride and t-butyl nitrite, and a combination of acetyl chloride and benzyltriethylammonium nitrite, which combinations are employed in an organic solvent such as dichloromethane.

Reaction conditions vary depending on the reagent employed. For example, when a combination of acetyl chloride and benzyltriethylammonium nitrite is employed as the reagent, in an organic solvent such as dichloromethane, benzyltriethylammonium nitrite (1 to 5 mol) is treated with acetyl chloride (1 to 5 mol) at −50° C. to room temperature for about 30 minutes to about three hours, and the resultant mixture is allowed to react with the compound [V] (1 mol) at −50° C. to room temperature for one hour to a few days. When the compound [V] is formed into a 2,6-dichloropurine derivative, the resultant derivative is treated with aqueous ammonia in an organic solvent such as dioxane or methanol.

The protective groups of the thus-obtained compound [VI] are removed, to thereby yield the compound of the present invention in which $R^2$ is hydrogen, and if desired, the compound is phosphorylated:

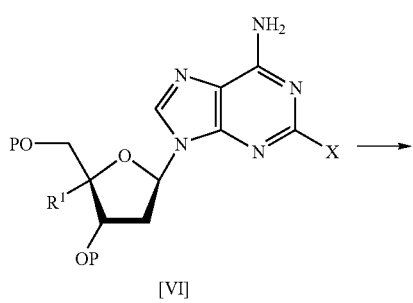

[VI]

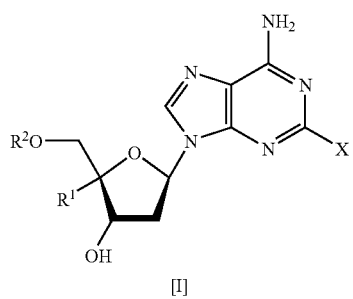

[I]

(wherein P represents a protective group, X represents a halogen atom, $R^1$ represents an ethynyl group or a cyano group, and $R^2$ represents hydrogen, a phosphate residue, or a phosphate derivative residue).

The protective groups may be removed through a technique which is appropriately selected from among typical techniques (e.g., hydrolysis under acidic conditions, hydrolysis under alkaline conditions, treatment with tetrabutylammonium fluoride, and catalytic reduction) in accordance with the protective groups employed.

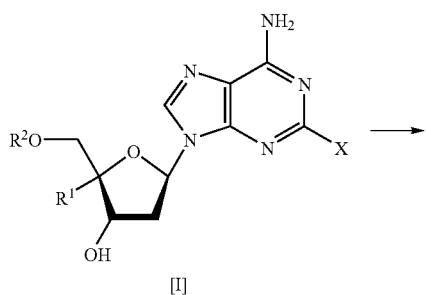

[I]

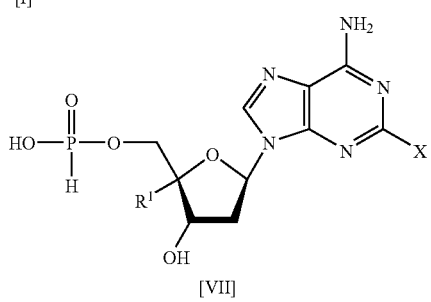

[VII]

(wherein X represents a halogen atom, $R^1$ represents an ethynyl group or a cyano group, and $R^2$ represents hydrogen).

In order to produce the 5'-H-phosphonate derivative [VII] (the compound of the present invention), the compound [I] in which $R^2$ is hydrogen and phosphonic acid are subjected to condensation in an organic solvent by use of an appropriate condensing agent. Examples of the organic solvent which may be employed include pyridine, and dimethylformamide in the presence of a base such as triethylamine. Examples of the condensing agent which may be employed include carbodiimides such as dicyclohexyl carbodiimide, diisopropyl carbodiimide, and water-soluble carbodiimide; sulfonic acid halides such as toluenesulfonyl chloride; and phosphate chlorides such as diphenyl phosphate chloride.

Reaction conditions vary depending on the reagent employed. For example, when dicyclohexyl carbodiimide is employed in pyridine, phosphonic acid (1 to 5 mol) and dicyclohexyl carbodiimide (1 to 10 mol) are added to 1 mol of the compound [1], and the resultant mixture is allowed to react at 0° C. to 50° C. for about one to about 24 hours.

When a compound in which $R^2$ is a monophosphate is to be produced, a compound in which $R^2$ is hydrogen is reacted with a phosphorylating agent; for example, phosphorus oxychloride or tetrachloropyrophosphoric acid, which selectively phosphorylates the 5'-position of a nucleoside. When a compound in which $R^2$ is a diphosphate or triphosphate is to be produced, the corresponding 5'-monophosphate compound is activated in the form of phosphoimidazolide, phosphomorpholidate, or anhydrous diphenylphosphate, and the thus-activated compound is reacted with phosphoric acid, pyrophosphoric acid, or a suitable salt thereof, to thereby produce a target compound in a free acid or salt form.

The compounds [II] of the present invention can be produced through the below-described steps.

First Step:

In the first step, the hydroxyl group at the 5'-position of a compound represented by formula [I] in which $R^2$ is hydrogen is selectively protected, to thereby yield a compound represented by formula [VIII]:

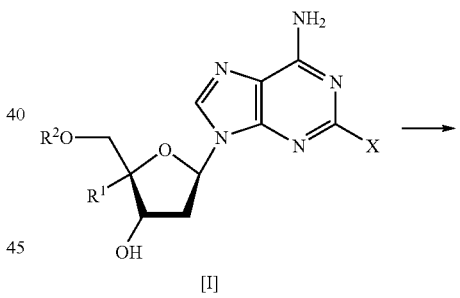

[I]

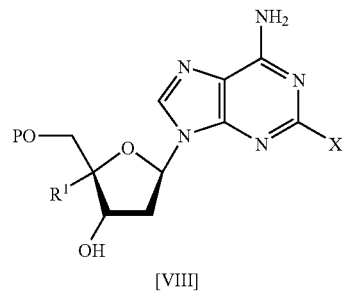

[VIII]

(wherein P represents a protective group, X represents a halogen atom, $R^1$ represents an ethynyl group or a cyano group, and $R^2$ represents hydrogen).

The protective group represented by P, which protects the hydroxyl group at the 5'-position, may be a protective group which is generally employed for selectively protecting a primary hydroxyl group. Specific examples of the protective group include a trimethoxytrityl group, a dimethoxytrityl group, a methoxytrityl group, a trityl group, a t-butyldimethylsilyl group, a t-butyldiphenylsilyl group, and a benzoyl group.

Introduction of the protective group can be carried out in a manner similar to that employed for the compound [V].

Second Step:

In the second step, the hydroxyl group at the 3'-position of the compound [VIII] is subjected to dehydration, forming a 2',3'-carbon-carbon double bond, to thereby yield a compound represented by formula [VIV].

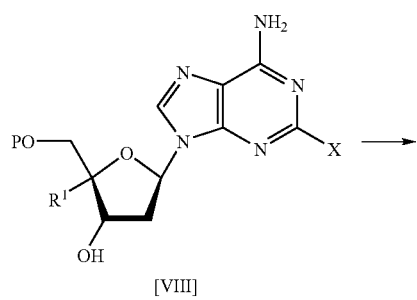

[VIII]

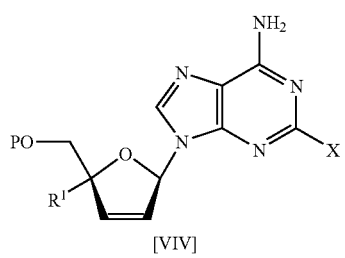

[VIV]

(wherein P represents a protective group, X represents a halogen atom, and $R^1$ represents an ethynyl group or a cyano group).

In order to produce the compound [VIV] through dehydration of the hydroxyl group at the 3'-position of the compound [VIII], the hydroxyl group at the 3'-position of the compound [VIII] is converted into a removable functional group such as a sulfonate group (e.g., a methanesulfonate group, a chloromethanesulfonate group, a toluenesulfonate group, or a trifluoromethanesulfonate group) or a halogen atom, and the thus-converted group is removed through treatment with a base.

Reaction conditions vary depending on the reagent employed. For example, in the case of reaction through formation of a trifluoromethanesulfonate, trifluoromethanesulfonic anhydride (1 to 5 mol) and a base (e.g., pyridine or triethylamine) (5 to 10 mol) are added to the compound [VIII] in an organic solvent such as dichloromethane or pyridine, and the resultant mixture is allowed to react at −78° C. to room temperature for about one to about 24 hours.

The protective group of the thus-obtained compound [VIV] is removed, to thereby yield the compound of the present invention in which $R^2$ is hydrogen, and if desired, the compound is phosphorylated:

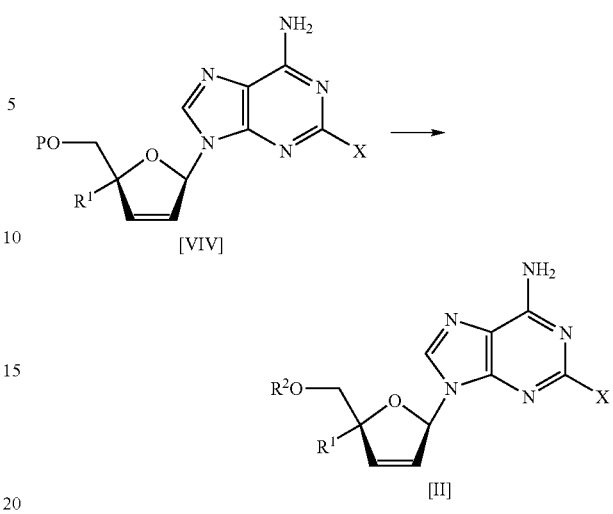

[VIV]

[II]

(wherein X represents a halogen atom, P represents a protective group, $R^1$ represents an ethynyl group or a cyano group, and $R^2$ represents hydrogen, a phosphate residue, or a phosphate derivative residue).

The protective group may be removed through a technique which is appropriately selected from among typical techniques (e.g., hydrolysis under acidic conditions, hydrolysis under alkaline conditions, treatment with tetrabutylammonium fluoride, and catalytic reduction) in accordance with the protective group employed.

A compound in which $R^2$ is a phosphate residue or a derivative thereof can be synthesized in a manner similar to that of the compound [I].

The compounds [III] of the present invention can be produced through the below-described steps.

First Step:

In the first step, the hydroxymethyl group at the 4-position of a compound represented by formula [X] is oxidized to thereby form an aldehyde group, which is further converted into a triethylsilylethynyl or cyano group to thereby yield a compound represented by formula [XI]:

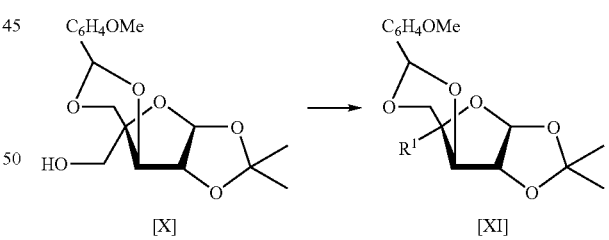

[X]

[XI]

(wherein $R^1$ represents an ethynyl group, a triethylsilylethynyl group, or a cyano group).

The compound [X] (i.e., starting material) is a known compound (Biosci. Biotech. Biochem., 57, 1433-1438 (1993)). The compound [X] can be converted into a triethylsilylethynyl compound through the following procedure: the hydroxymethyl group at the 4-position of the compound [X] is oxidized to form a formyl group, and the formyl group is converted into a dibromovinyl group, followed by removal of hydrogen bromide through treatment with a strong base.

When the hydroxymethyl group at the 4-position of the compound [X] is converted into a formyl group, an oxidizing agent is employed. Examples of the oxidizing agent which may be employed include chromium-containing oxidizing agents such as chromic anhydride-pyridine-acetic anhydride composite reagents, pyridinium chlorochromate, and pyridinium dichromate; high-valency iodine oxidizing agents such as Dess-Martin reagent; and dimethyl sulfoxide-based oxidizing agents such as a combination of dimethyl sulfoxide and acetic anhydride, oxalyl chloride, or dicyclohexyl carbodiimide.

Reaction conditions vary depending on the oxidizing agent to be employed. For example, when oxidation is carried out by use of oxalyl chloride and dimethyl sulfoxide, oxalyl chloride (1 to 5 mol) and dimethyl sulfoxide (1.5 to 6 mol) are added to 1 mol of the compound [X] in an organic solvent (e.g., dichloromethane), optionally under an inert gas atmosphere (e.g., argon or nitrogen), and the resultant mixture is allowed to react at −100° C. to 0° C. for about 15 minutes to about two hours. Subsequently, a base such as triethylamine is added in an amount of 2 to 10 mol to the mixture, and the resultant mixture is further allowed to react at room temperature for about 15 minutes to about two hours.

The thus-formed aldehyde can be converted into a corresponding alkyne through the following procedure: the aldehyde is subjected to carbon-increasing (i.e., C—C bond formation) reaction; the resultant compound is treated with a strong base to thereby form a metal alkynyl compound; and a protective group is introduced into the metal alkynyl compound. Carbon-increasing reaction is carried out in an organic solvent such as dichloromethane or dichloroethane, optionally under an inert gas atmosphere (e.g., argon or nitrogen). Specifically, carbon tetrabromide (1 to 5 mol) and triphenylphosphine (2 to 10 mol) are added to 1 mol of the above-formed aldehyde, and the resultant mixture is allowed to react at 0 to 50° C. for about 15 minutes to about three hours.

Treatment with a strong base can be carried out in an organic solvent such as tetrahydrofuran, 1,4-dioxane, or dimethoxyethane, optionally under an inert gas atmosphere (e.g., argon or nitrogen). Specifically, a lithium compound (e.g., methyllithium, n-butyllithium, or t-butyllithium) (2 to 4 mol) is added to 1 mol of the compound obtained through carbon-increasing reaction, and the resultant mixture is allowed to react at −100 to −20° C. for about five to about 60 minutes. Furthermore, when a silyl protective group is introduced into the alkynyl group of the thus-obtained compound, the aforementioned strong-base treatment is followed by addition of a silylating agent such as chlorotriethylsilane, and the resultant mixture is allowed to react.

Meanwhile, the compound [X] can be converted into a cyano compound through the following procedure: the hydroxymethyl group at the 4-position of the compound [X] is oxidized to form a formyl group, and the formyl group is converted into an oxime group, followed by dehydration of the thus-formed oxime group.

When the hydroxymethyl group at the 4-position of the compound [X] is converted into a formyl group, an oxidizing agent is employed. Examples of the oxidizing agent which may be employed include chromium-containing oxidizing agents such as chromic anhydride-pyridine-acetic anhydride composite reagents, pyridinium chlorochromate, and pyridinium dichromate; high-valency iodine oxidizing agents such as Dess-Martin reagent; and dimethyl sulfoxide-based oxidizing agents such as a combination of dimethyl sulfoxide and acetic anhydride, oxalyl chloride, or dicyclohexyl carbodiimide.

Reaction conditions vary depending on the oxidizing agent to be employed. For example, when oxidation is carried out by use of oxalyl chloride and dimethyl sulfoxide, oxalyl chloride (1 to 5 mol) and dimethyl sulfoxide (1.5 to 6 mol) are added to 1 mol of the compound [X] in an organic solvent (e.g., dichloromethane), optionally under an inert gas atmosphere (e.g., argon or nitrogen), and the resultant mixture is allowed to react at −100° C. to 0° C. for about 15 minutes to about two hours. Subsequently, a base such as triethylamine is added in an amount of 2 to 10 mol to the mixture, and the resultant mixture is further allowed to react at room temperature for about 15 minutes to about two hours.

The thus-formed aldehyde can be converted into a corresponding oxime by reacting 1 mol of the aldehyde with hydroxylamine hydrochloride (1 to 5 mol) in an organic solvent such as pyridine at room temperature to 100° C. for about 30 minutes to about three hours.

Dehydration of the thus-formed oxime can be carried out by use of a dehydrating agent (e.g., phosgene, carbonyldiimidazole, methanesulfonyl chloride, or acetic anhydride) in an organic solvent (e.g., dichloromethane, acetonitrile, or tetrahydrofuran) in the presence of a base (e.g., pyridine, triethylamine, or sodium acetate).

Dehydration conditions vary depending on the dehydrating agent to be employed. For example, when dehydration is carried out by use of methanesulfonyl chloride, in an organic solvent (such as dichloromethane, tetrahydrofuran, or pyridine), methanesulfonyl chloride (1 to 5 mol) and triethylamine (5 to 10 mol) are added to 1 mol of the oxime, and the resultant mixture is allowed to react at −50° C. to room temperature for about 15 minutes to about two hours.

Second Step:

In the second step, the methoxybenzylidene group which protects the hydroxyl groups at the 3- and 5-positions of the compound [XI] is removed, to thereby yield a compound represented by formula [XII]:

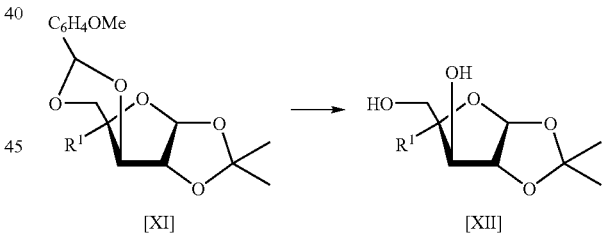

(wherein $R^1$ represents an ethynyl group, a triethylsilylethynyl group, or a cyano group).

The protective group may be removed through a technique which is appropriately selected from among typical techniques (e.g., hydrolysis under acidic conditions, and catalytic reduction).

Reaction conditions vary depending on the technique to be employed. For example, when the protective group is removed through hydrolysis under acidic conditions, the compound [XI] is allowed to react in an aqueous solution of an organic acid (e.g., formic acid or acetic acid) or mineral acid at 0 to 100° C. for one to 24 hours.

Third Step:

In the third step, the hydroxyl group at the 5-position of the compound [XII] is selectively protected, to thereby yield a compound represented by formula [XIII]:

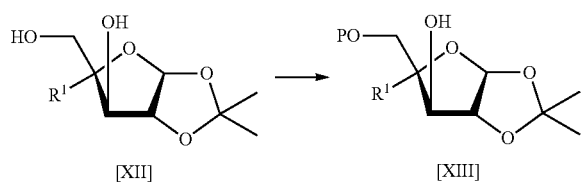

(wherein P represents a protective group, and R¹ represents an ethynyl group, a triethylsilylethynyl group, or a cyano group).

The protective group represented by P, which protects the hydroxyl group at the 5-position, may be a protective group which is generally employed for selectively protecting a primary hydroxyl group. Specific examples of the protective group include a trimethoxytrityl group, a dimethoxytrityl group, a methoxytrityl group, a trityl group, a t-butyldimethylsilyl group, a t-butyldiphenylsilyl group, and a benzoyl group.

Introduction of the protective group can be carried out in a manner similar to that employed for the compound [V].

Fourth Step:

In the fourth step, the hydroxyl group at the 3-position of the compound [XIII] is reduced, to thereby yield a compound represented by formula [XIV]:

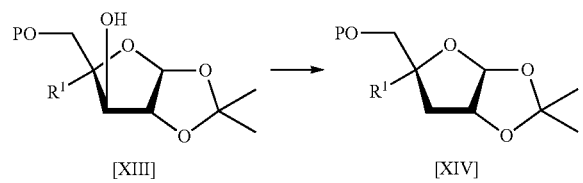

(wherein P represents a protective group, and R¹ represents an ethynyl group, a triethylsilylethynyl group, or a cyano group).

Deoxygenation of the hydroxyl group at the 3-position can be carried out by converting the compound having the hydroxyl group into a corresponding halide (iodite, bromide or chloride), phenoxythionocarbonate, thiocarbonylimidazole, or methyldithiocarbonate, and by reducing the thus-converted compound by use of a radical reducing agent in the presence of a radical initiator.

For example, when deoxygenation is carried out through formation of a phenoxythiocarbonyl compound, conversion of the hydroxyl group to a phenoxythiocarbonyl group is carried out in an organic solvent (e.g., tetrahydrofuran, acetonitrile, or dichloromethane) in the presence of a base such as dimethylaminopyridine or pyridine, optionally under an inert gas atmosphere such as argon or nitrogen. Specifically, a phenyl chlorothionoformate derivative (1 to 10 mol, preferably 1 to 2 mol) is added to 1 mol of the aforementioned compound in which only the protective group for the hydroxyl group at the 3-position has been eliminated, and the resultant mixture is allowed to react under stirring at 0 to 5° C. for about 0.5 to about five hours.

Subsequently, reduction is carried out in an organic solvent (e.g., toluene or benzene) in the presence of a radical initiator such as azobisisobutyronitrile, optionally under an inert gas atmosphere such as argon or nitrogen. Specifically, a radical reducing agent such as tributyltin hydride or tris(trimethylsilyl)silane (1 to 10 mol, preferably 2 to 5 mol) is added to 1 mol of the aforementioned phenoxythiocarbonyl compound, and the resultant mixture is allowed to react under stirring at 50 to 150° C. for about one to about five hours.

Fifth Step:

In the fifth step, the isopropylidene group at the 1- and 2-positions of the compound [XIV] is removed, and then the thus-formed hydroxyl groups are acetylated, to thereby yield a compound represented by formula [XV]:

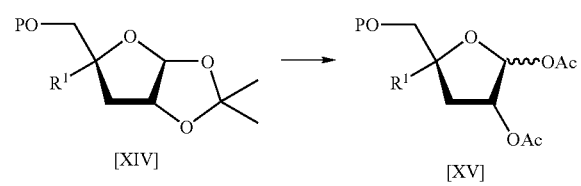

(wherein P represents a protective group, and R¹ represents an ethynyl group, a triethylsilylethynyl group, or a cyano group).

When the isopropylidene group at the 1- and 2-positions is removed through hydrolysis under acidic conditions, the compound [XIV] is allowed to react in an aqueous solution of an organic acid (e.g., formic acid or acetic acid) or mineral acid at 0 to 100° C. for one to 24 hours.

Introduction of acetyl groups to the hydroxyl groups, which follows removal of the isopropylidene group, can be carried out by means of a customary technique. For example, acetyl groups are introduced to the hydroxyl groups through reaction with an acetylating agent (e.g., acetyl chloride or acetic anhydride) in an organic solvent such as pyridine, acetonitrile, or dichloromethane in the presence of a base such as pyridine or triethylamine.

For example, in the case of reaction in pyridine by use of acetic anhydride, acetic anhydride (2 to 10 mol) and, if desired, a catalytic amount of 4-dimethylaminopyridine are added to 1 mol of the compound from which the isopropylidene group has been removed, and the resultant mixture is allowed to react at 0 to 100° C. for one to 24 hours.

Sixth Step:

In the sixth step, the compound [XV] and 2,6-diaminopurine are subjected to condensation, to thereby yield a compound represented by formula [XVI]:

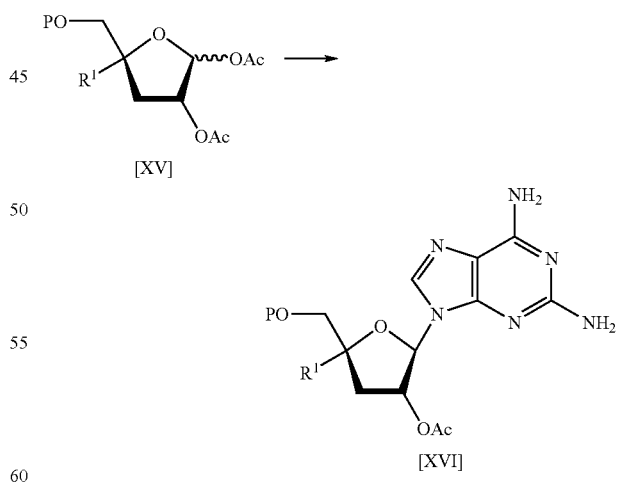

(wherein P represents a protective group, and R¹ represents an ethynyl group, a triethylsilylethynyl group, or a cyano group).

Condensation of the compound [XV] and 2,6-diaminopurine can be carried out by reacting the compound [XV] with 2,6-diaminopurine in the presence of a Lewis acid. In this case, 2,6-diaminopurine may be silylated, and such silylation of 2,6-diaminopurine may be carried out through a known technique. For example, 2,6-diaminopurine is silylated under reflux in a mixture of hexamethyldisilazane and trimethylchlorosilane, or is silylated under reflux by use of bis(trimethylsilyl)acetamide in an organic solvent such as acetonitrile or 1,2-dichloroethane. Examples of Lewis acids to be employed include trimethylsilyl trifluoromethanesulfonate, tin tetrachloride, zinc chloride, zinc iodide, and anhydrous aluminum chloride.

Condensation reaction can be carried out in an organic solvent such as dichloromethane, 1,2-dichloroethane, acetonitrile, or toluene, optionally under an inert gas atmosphere such as argon or nitrogen. Specifically, 2,6-diaminopurine (1 to 10 mol) and a Lewis acid (0.1 to 10 mol) are added to 1 mol of the compound [XV], and the resultant mixture is allowed to react at −20 to 150° C. for about 30 minutes to about 24 hours.

Seventh Step:

In the seventh step, the amino group at the 2-position of the compound [XVI] is converted into halogen atom, to thereby yield a compound represented by formula [XVII]:

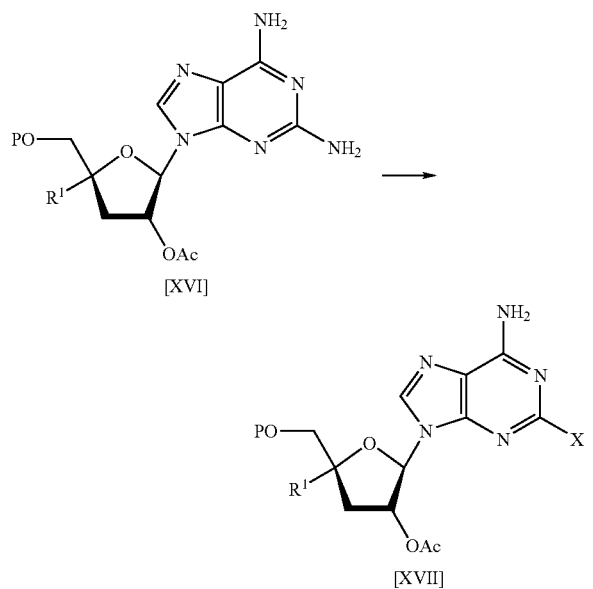

[XVI]

[XVII]

(wherein P represents a protective group, X represents a halogen atom, and $R^1$ represents an ethynyl group, a triethylsilylethynyl group, or a cyano group).

The compound [XVII] can be synthesized through the following procedure: after the amino group at the 2-position of the compound [XVI] is treated with a nitrite derivative, halogen atom is introduced at the 2-position of a base moiety by use of a halogen reagent; or the amino groups at the 2- and 6-positions are treated under the same conditions, thereby forming a 2,6-dihalopurine derivative, and the halogen atom at the 6-position of base moiety is converted into an amino group through treatment with ammonia.

Examples of reagents for substituting the amino group at the 2-position of the compound [XVI] by fluorine include sodium nitrite in tetrafluoroboric acid; and a nitrous acid ester (e.g., t-butyl nitrite) in hydrogen fluoride-pyridine.

Reaction conditions vary depending on the reagent employed. For example, when t-butyl nitrite is employed in hydrogen fluoride-pyridine, t-butyl nitrite (1 to 3 mol) is added to the compound [XVI] in hydrogen fluoride-pyridine serving as a solvent, and the resultant mixture is allowed to react at −50° C. to 0° C. for about 15 minutes to about five hours. When the compound [XVI] is formed into a 2,6-difluoropurine derivative, the resultant derivative is treated with aqueous ammonia in an organic solvent such as dioxane or methanol.

Examples of reagents for substituting the amino group at the 2-position of the compound [XVI] by chlorine include a combination of antimony trichloride and t-butyl nitrite, and a combination of acetyl chloride and benzyltriethylammonium nitrite, which combinations are employed in an organic solvent such as dichloromethane.

Reaction conditions vary depending on the reagent employed. For example, when a combination of acetyl chloride and benzyltriethylammonium nitrite is employed as the reagent, in an organic solvent such as dichloromethane, benzyltriethylammonium nitrite (1 to 5 mol) is treated with acetyl chloride (1 to 5 mol) at −50° C. to room temperature for about 30 minutes to about three hours, and the resultant mixture is allowed to react with 1 mol of the compound [XVI] at −50° C. to room temperature for one hour to a few days. When the compound [XVI] is formed into a 2,6-dichloropurine derivative, the resultant derivative is treated with aqueous ammonia in an organic solvent such as dioxane or methanol.

Eighth Step:

In the eighth step, the acetyl group which protects the hydroxyl group at the 2'-position of the compound [XVII] is removed, to thereby yield a compound represented by formula [XVIII]:

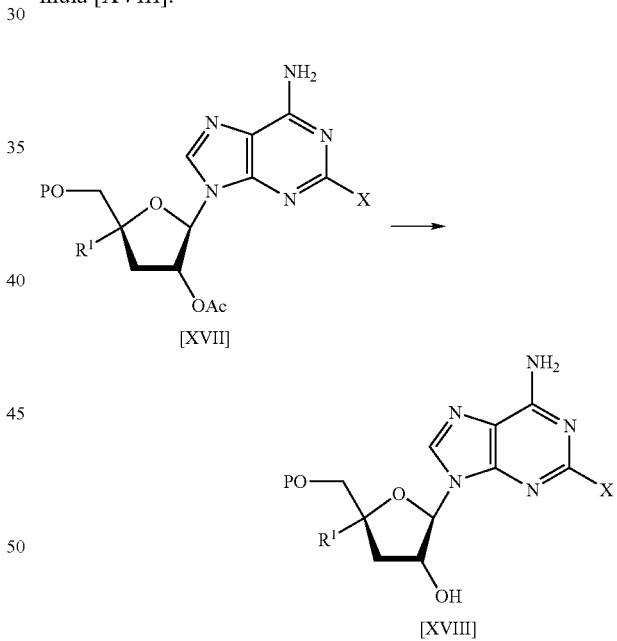

[XVII]

[XVIII]

(wherein P represents a protective group, X represents a halogen atom, and $R^1$ represents an ethynyl group, a triethylsilylethynyl group, or a cyano group).

The acetyl group can be removed by use of an appropriate base or acid catalyst. For example, when removal of the acetyl group is carried out in a solvent mixture of water and an alcohol (e.g., ethanol), a base catalyst such as sodium hydroxide, potassium hydroxide, triethylamine, or aqueous ammonia can be employed.

For example, the acetyl group can be removed by allowing the compound [XVII] to react by use of aqueous ammonia in methanol at 0 to 100° C. for one to 24 hours.

Ninth Step:

In the ninth step, the hydroxyl group at the 2'-position of the compound [XVIII] is reduced, to thereby yield a compound represented by formula [XIX]:

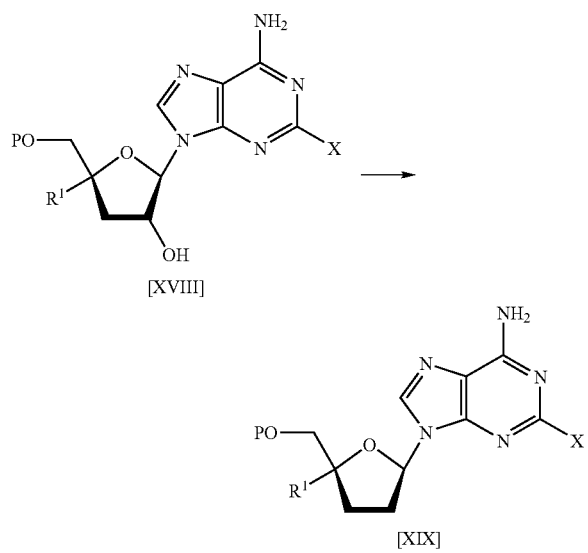

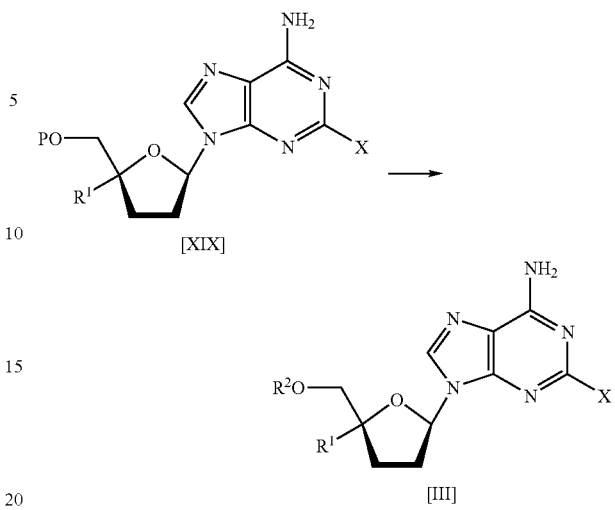

(wherein P represents a protective group, X represents a halogen atom, and $R^1$ represents an ethynyl group, a triethylsilylethynyl group, or a cyano group).

Deoxygenation of the hydroxyl group at the 3-position can be carried out by converting the compound having the hydroxyl group into the corresponding halide (iodite, bromide or chloride), phenoxythionocarbonate, thiocarbonylimidazole, or methyldithiocarbonate, and by reducing the thus-converted compound by use of a radical reducing agent in the presence of a radical initiator.

For example, when deoxygenation is carried out through formation of a phenoxythiocarbonyl compound, conversion of the hydroxyl group to a phenoxythiocarbonyl group is carried out in an organic solvent (e.g., tetrahydrofuran, acetonitrile, or dichloromethane) in the presence of a base such as dimethylaminopyridine or pyridine, optionally under an inert gas atmosphere such as argon or nitrogen. Specifically, a phenyl chlorothionoformate derivative (1 to 10 mol, preferably 1 to 2 mol) is added to 1 mol of the aforementioned compound in which only the protective group for the hydroxyl group at the 2'-position has been eliminated, and the resultant mixture is allowed to react under stirring at 0 to 50° C. for about 0.5 to about five hours.

Subsequently, reduction is carried out in an organic solvent (e.g., toluene or benzene) in the presence of a radical initiator such as azobisisobutyronitrile, optionally under an inert gas atmosphere such as argon or nitrogen. Specifically, a radical reducing agent such as tributyltin hydride or tris(trimethylsilyl)silane (1 to 10 mol, preferably 2 to 5 mol) is added to 1 mol of the aforementioned phenoxythiocarbonyl compound, and the resultant mixture is allowed to react under stirring at 50 to 150° C. for about one to about five hours.

The protective group for the hydroxyl group of the thus-obtained compound [XIX] is removed, to thereby yield the compound of the present invention in which $R^2$ is hydrogen, and if desired, the compound is phosphorylated:

(wherein P represents a protective group, X represents a halogen atom, $R^1$ represents an ethynyl group, a triethylsilylethynyl group, or a cyano group, and $R^2$ represents hydrogen, a phosphate residue, or a phosphate derivative residue).

The protective group may be removed through a technique which is appropriately selected from among typical techniques (e.g., hydrolysis under acidic conditions, hydrolysis under alkaline conditions, treatment with tetrabutylammonium fluoride, and catalytic reduction) in accordance with the protective group employed.

A compound in which $R^2$ is a phosphate residue or a derivative thereof can be synthesized in a manner similar to that of the compound [I].

The compounds of the present invention may be isolated and purified through conventional methods, in appropriate combination, which are employed for isolating and purifying nucleosides and nucleotides; for example, recrystallization, ion-exchange column chromatography, and adsorption column chromatography. The thus-obtained compounds may further be converted to salts thereof in accordance with needs.

(3) Use

As shown in the below-described Test Examples, the compounds of the present invention exhibit excellent antiviral activity against retroviruses. Thus, compositions of the present invention containing one of the compounds of the present invention as an active ingredient find utility in the field of therapeutic drugs. Specifically, the compositions of the present invention are useful for the treatment of infectious diseases caused by a retrovirus, in particular, AIDS, which is caused by HIV infection.

The dose of the compounds of the present invention depends on and is determined in consideration of conditions such as the age, body weight, and type of disease of the patient; the severity of the disease; the drug tolerance; and the administration route. However, the daily dose is determined to fall typically within 0.00001-1,000 mg/kg, preferably 0.0001-100 mg/kg body weight. The compounds are administered in a single dose or divided doses.

Any administration route may be employed, and the compounds may be administered orally, parenterally, enterally, or topically.

When a pharmaceutical is prepared from the compounds of the present invention, the compounds are typically mixed with customarily employed additives, such as a carrier and an excipient. Examples of solid carriers include lactose, kaolin, sucrose, crystalline cellulose, corn starch, talc, agar, pectin, stearic acid, magnesium stearate, lecithin, and sodium chloride. Examples of liquid carriers include glycerin, peanut oil, polyvinylpyrrolidone, olive oil, ethanol, benzyl alcohol, propylene glycol, and water.

The product form is arbitrarily selected. When the carrier is solid, examples of product forms include tablets, powder, granules, capsules, suppositories, and troches, whereas when it is liquid, examples include syrup, emulsion, soft-gelatin-capsules, cream, gel, paste, spray, and injection.

EXAMPLES

The present invention will next be described in detail by way of examples including Synthesis Examples, Test Examples, and Drug Preparation Examples, which should not be construed as limiting the invention thereto.

Synthesis Example 1

Synthesis of 2'-deoxy-4'-C-ethynyl-2-fluoroadenosine (compound 4)

(1) Synthesis of 9-(3,5-di-O-acetyl-2-deoxy-4-C-ethynyl-β-D-ribo-pentofuranosyl)-2,6-diaminopurine (compound 2)

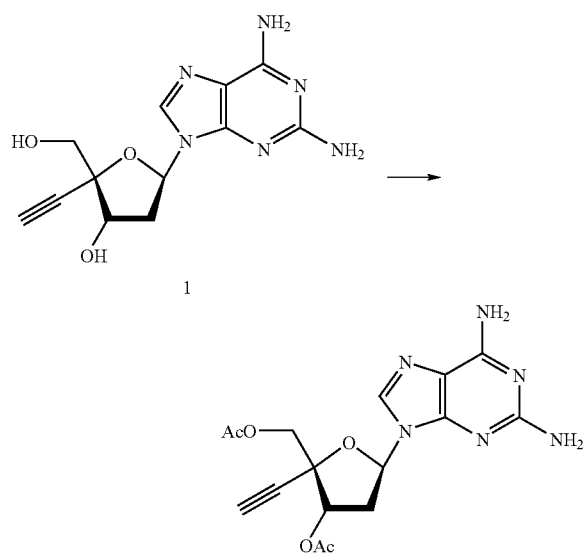

Compound 1 (0.33 g, 1.14 mmol) was suspended in acetonitrile (10.0 ml), and acetic anhydride (0.23 ml, 2.43 mmol), triethylamine (0.67 g, 4.81 mmol), and a small amount of 4-dimethylaminopyridine were added to the resultant suspension, followed by stirring at room temperature overnight.

The thus-precipitated crystals were filtered and dried, to thereby yield compound 2 (0.40 g, 1.07 mmol, 93.9%).

$^1$H-NMR (DMSO-$d_6$)δ7.94(1H, s, H-8), 6.76(2H, bs, NH$_2$), 6.27(1H, t, H-1', J=7.00), 5.84(2H, bs, NH$_2$), 5.60(1H, dd, H-3', J=4.00, 6.80), 4.46(1H, d, H-5'a, J=11.5), 4.21(1H, d, H-5'b, J=11.5), 3.74(1H, s, ethynyl) 3.12(1H, m, H-2'a), 2.52(1H, m, H-2'b), 2.12, 2.03(each 3H, s, acetyl)

(2) Synthesis of 3',5'-di-O-acetyl-2'-deoxy-4'-C-ethynyl-2-fluoroadenosine (compound 3)

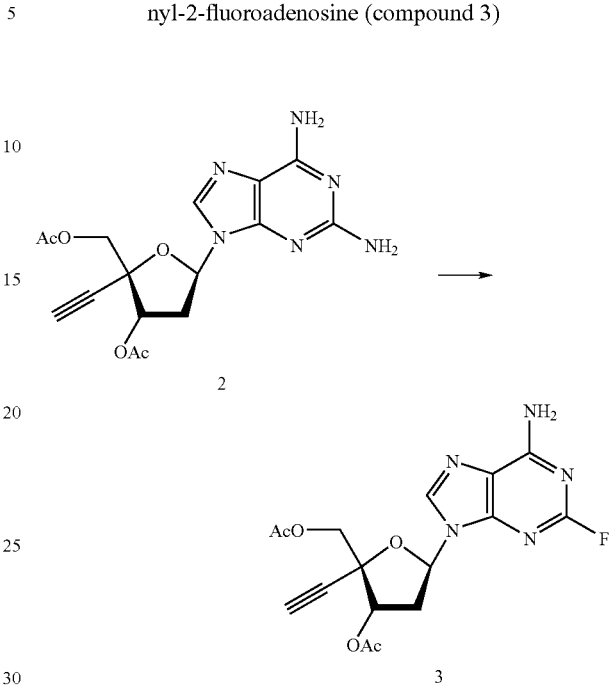

Compound 2 (450 mg, 1.20 mmol) was dissolved in 70% hydrogen fluoride-pyridine (5.00 ml), and t-butyl nitrite (0.194 ml, 1.63 mmol) was added to the resultant solution, followed by stirring at −10° C. for one hour. Distilled water was added to the resultant mixture, and the resultant mixture was subjected to extraction with chloroform. The resultant organic layer was dried over anhydrous magnesium sulfate, and then concentrated under reduced pressure. A mixture of chloroform and methanol (50:1) was added to the resultant residue, and the thus-precipitated crystals were filtered and dried, to thereby yield compound 3 (240 mg, 0.64 mmol, 53.3%).

$^1$H-NMR (DMSO-$d_6$) δ8.34(1H, s, H-8), 7.94, 7.99(each 1H, bs, NH$_2$), 6.35(1H, t, H-1', J=6.80), 5.68(1H, dd, H-3', J=5.10, 7.05), 4.41(1H, d, H-5'a, J=11.6), 4.21(1H, d, H-5'b, J=11.6), 3.42(1H, s, ethynyl), 3.14(1H, m, H-2'a), 2.63(1H, m, H-2'b), 2.12, 2.00(each 3H, s, acetyl).

(3) Synthesis of 2'-deoxy-4'-C-ethynyl-2-fluoroadenosine (compound 4)

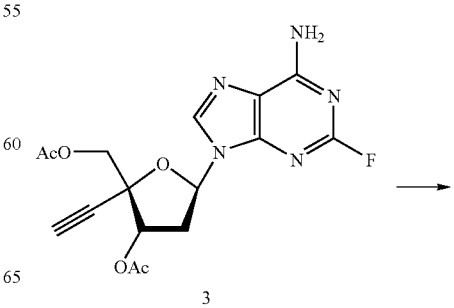

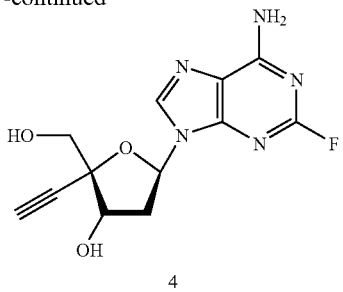

4

Compound 3 (200 mg, 0.53 mmol) was dissolved in methanol (7.00 ml), and 28% aqueous ammonia (5.00 ml) was added to the resultant solution, followed by stirring at room temperature for four hours. The resultant reaction mixture was concentrated under reduced pressure, and a mixture of chloroform and methanol (20:1) was added to the resultant residue. The thus-precipitated crystals were filtered, and then the resultant crystals were recrystallized from water, to thereby yield compound 4 (113 mg, 0.39 mmol, 73.6%).

$^1$H-NMR (DMSO-$d_6$) δ8.30(1H, s, H-8), 7.87, 7.84(each 1H, bs, NH$_2$), 6.24(1H, dd, H-1', J=5.05, 7.15), 5.57(1H, d, 3'-OH, J=5.50), 5.30(1H, t, 5'-OH, J=6.40), 4.57(1H, m, H-3'), 3.65(1H, m, H-5'a), 3.55(1H, m, H-5'b), 3.51(1H, s, ethynyl), 2.70(1H, m, H-2'a), 2.44(1H, m, H-2'b).

Synthesis Example 2

Synthesis of 4'-C-cyano-2'-deoxy-2-fluoroadenosine (compound 8)

(1) Synthesis of 9-(3,5-di-O-acetyl-4-C-cyano-2-deoxy-β-D-ribo-pentofuranosyl)-2,6-diaminopurine (compound 6)

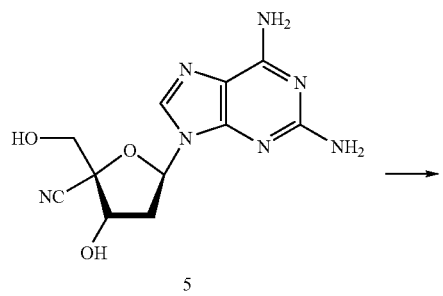

5

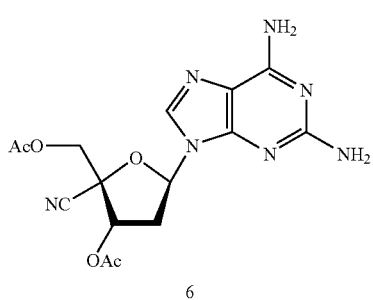

6

Compound 5 (122 mg, 0.418 mmol) was suspended in acetonitrile (5.00 ml), and acetic anhydride (118 μl, 1.25 mmol), triethylamine (352 μL, 2.51 mmol), and a small amount of 4-dimethylaminopyridine were added to the resultant suspension, followed by stirring at room temperature overnight. The thus-precipitated crystals were filtered and dried, to thereby yield compound 6 (128 mg, 0.341 mmol, 81.6%).

$^1$H-NMR (CDCl$_3$) δ7.54(1H, s, H-8), 6.31(1H, t, H-1', J=7.00), 6.06(1H, dd, H-3', J=5.00, 6.50), 5.31(2H, bs, NH$_2$), 4.95(1H, d, H-5'a, J=11.5), 4.80(2H, bs, NH$_2$), 4.37(1H, d, H-5'b, J=12.0), 3.43(1H, m, H-2'a), 2.63(1H, m, H-2'b), 2.23, 2.12(each 3H, s, acetyl).

(2) Synthesis of 3',5'-di-O-acetyl-4'-C-cyano-2'-deoxy-2-fluoroadenosine (compound 7)

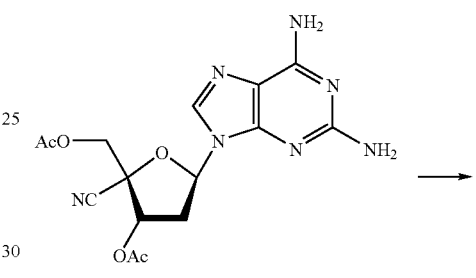

6

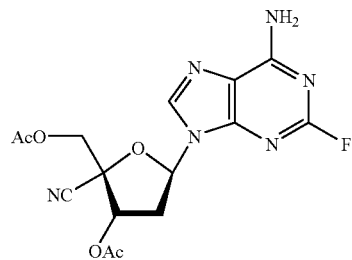

7

Compound 6 (118 mg, 0.314 mmol) was dissolved in 70% hydrogen fluoride-pyridine (2.30 ml), and t-butyl nitrite (50.0 μl, 0.427 mmol) was added to the resultant solution, followed by stirring at −10° C. for three hours. To the resultant mixture, t-butyl nitrite (10.0 μl, 85 μmol) was further added, and then the mixture was further stirred at −10° C. for one hour. After a saturated aqueous solution of sodium bicarbonate was added to the resultant mixture, the resultant mixture was subjected to extraction with ethyl acetate, and the resultant organic layer was washed with a saturated aqueous solution of sodium chloride. The resultant organic layer was dried over magnesium sulfate, and then concentrated under reduced pressure. The resultant residue was dissolved in ethanol under heating, followed by cooling. The thus-precipitated crystals were filtered and dried, to thereby yield compound 7 (53.7 mg, 0.14 mmol, 45.2%).

$^1$H-NMR-(DMSO-$d_6$)δ8.35(1H, s, H-8), 8.00, 7.92(each 1H, bs, NH$_2$), 6.54(1H, t, H-1', J=7.00), 5.83(1H, dd, H-3', J=4.00, 6.50), 4.63(1H, d, H-5'a, J=11.5), 4.44(1H, d, H-5'b, J=12.0), 3.26(1H, m, H-2'a), 2.73(1H, m, H-2'b), 2.18, 2.05 (each 3H, s, acetyl).

(3) Synthesis of 4'-C-cyano-2'-deoxy-2-fluoroadenosine (compound 8)

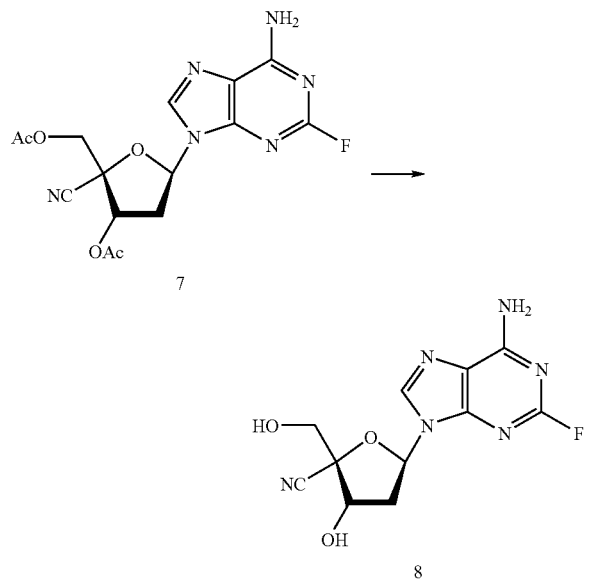

Compound 7 (53.7 mg, 9.142 mmol) was dissolved in methanol (1.90 ml), and 28% aqueous ammonia (1.30 ml) was added to the resultant solution, followed by stirring at room temperature for 30 minutes. The resultant reaction mixture was concentrated under reduced pressure, and then the resultant residue was purified by means of silica gel column chromatography (silica gel 10 ml, hexane/ethyl acetate (5:1), ethyl acetate, ethyl acetate/methanol (10:1)), to thereby yield compound 8 (30.2 mg, 0.10 mmol, 72.3%).

$^1$H-NMR (DMSO-d$_6$) δ8.31(1H, s, H-8), 7.93, 7.82(each 1H, bs, NH$_2$), 6.43(1H, t, H-1', J=7.00), 6.36(1H, bs, 3'-OH), 5.74(1H, bs, 5'-OH), 4.70(1H, t, H-3', J=5.50), 3.80(1H, d, H-5'a, J=12.0), 3.65(1H, d, H-5'b, J=12.0), 2.93(1H, m, H-2'a), 2.47(1H, m, H-2'b).

Synthesis Example 3

Synthesis of 2-chloro-2'-deoxy-4'-C-ethynyladenosine (compound 9)

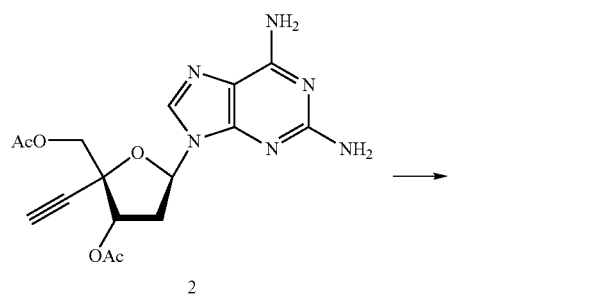

-continued

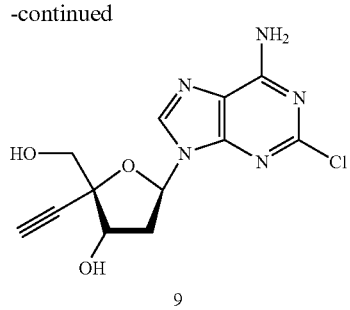

Benzyltriethylammonium nitrite (1.04 g, 4.36 mmol) was dissolved in dichloromethane (24.0 ml), and acetyl chloride (0.40 ml, 5.63 mmol) was added to the resultant solution, followed by stirring at 0° C. for 30 minutes. To the resultant solution, a solution of compound 2 (340 mg, 0.91 mmol) in dichloromethane (6.00 ml) was added, and the resultant mixture was stirred at 0° C. for three hours. The resultant reaction mixture was diluted with chloroform, and subsequently the resultant organic layer was washed with water, dried over anhydrous magnesium sulfate, and concentrated under reduced pressure. To the resultant residue, 28% aqueous ammonia (10.0 ml) and methanol (15.0 ml) were added, and the resultant mixture was stirred at room temperature overnight. Thereafter, the resultant reaction mixture was concentrated under reduced pressure, and the resultant residue was purified by means of silica gel column chromatography (silica gel 50 ml, chloroform:methanol=20:1 to 10:1). The thus-purified residue was further purified by means of ODS column chromatography (ODS 50 ml, 5 to 10 to 15 to 20% acetonitrile), to thereby yield compound 9 (39.2 mg, 0.13 mmol, 14.3%).

$^1$H-NMR (DMSO-d$_6$) δ8.34(1H, s, H-8), 7.84(2H, bs, NH$_2$), 6.27(1H, dd, H-1', J=5.00, 7.00), 5.60(1H, d, 3'-OH, J=5.00), 5.33(1H, t, 5'-OH, J=6.00), 4.56(1H, m, H-3'), 3.64 (1H, m, H-5'a), 3.56(1H, m, H-5'b), 3.52(1H, s, ethynyl), 2.68(1H, m, H-2'a), 2.45(1H, m, H-2'b).

Synthesis Example 4

Synthesis of 2'-deoxy-4'-C-ethynyl-2-fluoroadenosine 5'-H-phosphonate (compound 10)

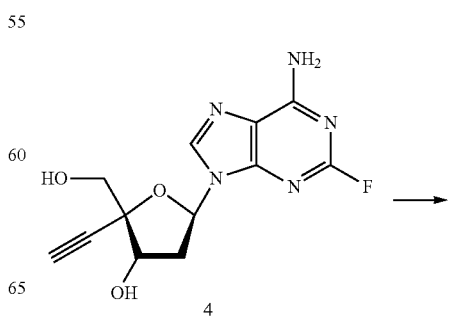

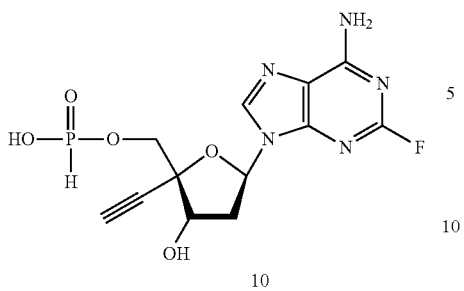

10

Compound 4 (50.0 mg, 0.171 mmol) was dissolved in pyridine (2.00 ml), and phosphonic acid (21.0 mg, 0.25 mmol) and dicyclohexyl carbodiimide (10.6 mg, 0.51 mmol) were added to the resultant solution, followed by stirring at room temperature for five hours. The resultant precipitate was removed through filtration, and then the filtrate was concentrated under reduced pressure. The resultant residue was partitioned with water and chloroform. The resultant aqueous layer was concentrated under reduced pressure, and the thus-obtained residue was purified by means of preparative thin-layer chromatography (isopropanol:28% aqueous ammonia:water=7:1:2). The resultant residue was co-boiled with acetonitrile, and then treated with methanol and ether, to thereby yield a powdery compound (compound 10; 6.3 mg, 17.6 µmol, 10.3%).

$^1$H-NMR (D$_2$O) δ8.13(1H, s, H-8), 6.49(1H, d, H—P, J=645), 6.25(1H, dd, H-1', J=5.00, 7.50), 3.96(2H, m, H-5'), 2.75, 2.59(each 1H, m, H-2').

$^{31}$P-NMR (D$_2$O)δ6.45.

Synthesis Example 5

Synthesis of 2',3'-didehydro-2',3'-dideoxy-4'-C-ethynyl-2-fluoroadenosine (compound 13)

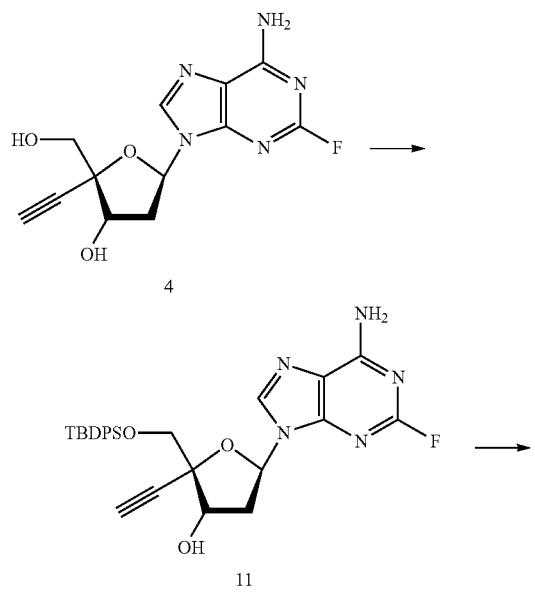

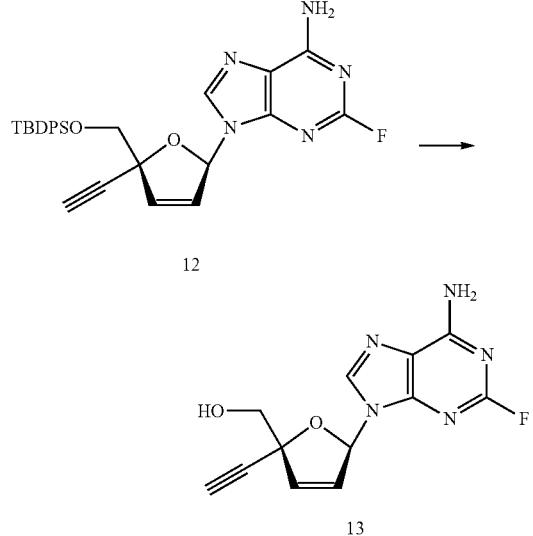

Compound 4 (0.28 g, 0.95 mmol) was dissolved in dimethylformamide (7.00 ml), and t-butylchlorodiphenylsilane (0.50 ml, 1.92 mmol) and imidazole (0.26 g, 3.82 mmol) were added to the resultant solution, followed by stirring at room temperature overnight. After methanol was added to the resultant reaction mixture, the resultant mixture was concentrated under reduced pressure, and the resultant residue was partitioned with ethyl acetate and water. The resultant organic layer was dried over anhydrous magnesium sulfate, and then concentrated under reduced pressure. The thus-obtained residue was purified by means of silica gel column chromatography (silica gel 100 ml, chloroform:methanol=20:1), to thereby yield crude compound 11 (0.38 g).

The crude compound 11 (0.38 g) was dissolved in dichloromethane (10.0 ml), and trifluoromethanesulfonic anhydride (0.14 ml, 0.83 mmol) and pyridine (0.14 g, 1.71 mmol) were added to the resultant solution at −10° C., followed by stirring at the same temperature for two hours. A saturated aqueous solution of sodium bicarbonate was added to the resultant reaction mixture, and then the resultant mixture was subjected to extraction with chloroform. The resultant organic layer was dried over anhydrous magnesium sulfate, and then concentrated under reduced pressure. The thus-obtained crude triflate was employed in the next reaction without purification thereof.

The crude triflate was dissolved in dry tetrahydrofuran (20.0 ml), and a solution of 1-M sodium hexamethyldisilazide in tetrahydrofuran (2.50 ml, 2.50 mmol) was added to the resultant solution in an argon atmosphere at −78° C., followed by stirring at the same temperature for two hours. Thereafter, the resultant reaction mixture was allowed to warm to room temperature, and then stirred overnight. Water was added to the resultant reaction mixture, and then the resultant mixture was subjected to extraction with ethyl acetate. The resultant organic layer was dried over anhydrous magnesium sulfate, and then concentrated under reduced pressure. The thus-obtained residue was purified by means of silica gel column chromatography (silica gel 50 ml, chloroform:methanol=50:1 to 20:1), to thereby yield crude compound 12 (0.20 g).

The thus-obtained crude compound 12 was dissolved in tetrahydrofuran (10.0 ml), and a solution of 1-M tetrabutylammonium fluoride in tetrahydrofuran (0.59 ml, 0.59 mmol) was added to the resultant solution, followed by stirring at room temperature for 30 minutes. The resultant reaction mixture was concentrated under reduced pressure, and then a mixture of chloroform and methanol (10:1) was added to the thus-concentrated mixture. The thus-precipitated crystals were filtered, to thereby yield compound 13 (52.0 mg, 0.19 mmol, 20.0% from compound 4).

$^1$H-NMR (DMSO-$d_6$) δ8.08(1H, s, H-8), 7.84(2H, bs, NH$_2$), 6.90(1H, t, H-1', J=1.50), 6.43(1H, dd, H-3', J=2.00, 6.00), 6.27(1H, dd, H-3', J=1.00, 6.00), 5.37(1H, t, 5'-OH, J=6.00), 3.71(1H, s, ethynyl), 3.67(1H, dd, H-5'a, J=6.00, 12.0), 3.57(1H, dd, H-5'b, J=6.00, 12.0).

Synthesis Example 6

Synthesis of 2',3'-didehydro-2',3'-dideoxy-4'-C-ethynyl-2-fluoroadenosine 5'-H-phosphonate (compound 14)

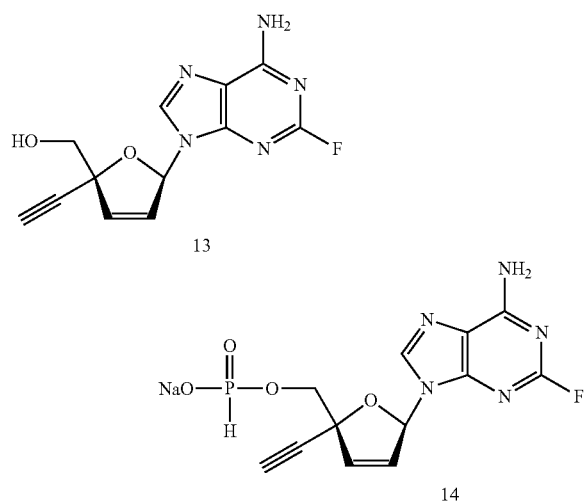

Compound 13 (13.0 mg, 0.047 mmol) was dissolved in pyridine (0.7 ml), and phosphonic acid (7.7 mg, 0.094 mmol) and dicyclohexyl carbodiimide (29.2 mg, 0.14 mmol) were added to the resultant solution, followed by stirring at room temperature for one hour. The resultant reaction mixture was concentrated under reduced pressure, and the thus-obtained residue was purified by means of ODS column chromatography (ODS 10 ml, 0 to 1% acetonitrile). The resultant residue was applied to a Dowex 50Wx8 column (Na type) and eluted. The eluate was concentrated, and the resultant residue was treated with methanol and ether, to thereby yield a powdery compound (compound 14; 4.3 mg, 12 μmol, 25.5%).

$^1$H-NMR (MeOD) δ8.30(1H, s, H-8), 6.69(1H, d, H—P, J=625), 7.02(1H, bt, H-1'), 6.48(1H, dd, H-2', J=2.00, 5.50), 6.22(1H, dd, H-3', J=1.00, 5.50), 4.18(1H, dd, H-5'a, J=7.50, 11.0), 3.99(1H, dd, H-5'b, J=7.50, 11.0).

$^{31}$P-NMR (MeOD) δ4.11.

Synthesis Example 7

Synthesis of 2',3'-dideoxy-4'-C-ethynyl-2-fluoroadenosine (compound 23)

(1) Synthesis of 1,2-O-isopropylidene-4-C-triethylsilylethynyl-α-D-xylo-pentofuranose (compound 16)

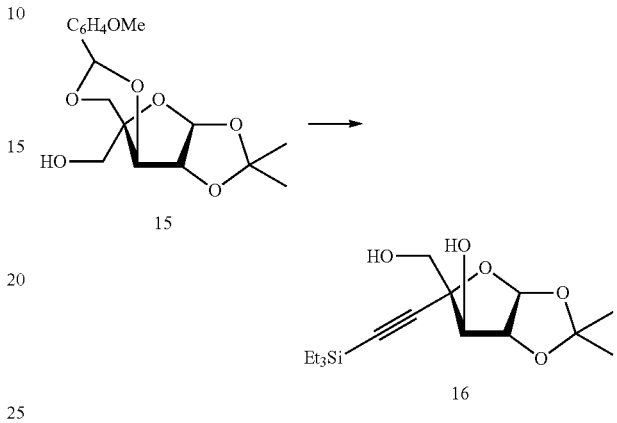

Oxalyl chloride (0.54 ml, 6.19 mmol) was dissolved in dichloromethane (10.0 ml), and then dimethyl sulfoxide (0.90 ml, 12.7 mmol) was added dropwise to the resultant solution at −60° C., followed by stirring at the same temperature for 15 minutes. A solution of compound 15 (1.06 g, 3.13 mmol, Biosci. Biotech. Biochem., 57, 1433-1438 (1993)) in dichloromethane (15.0 ml) was added dropwise to the resultant mixture, followed by stirring at −60° C. for 30 minutes. After triethylamine (1.86 ml, 13.3 mmol) was added thereto, the resultant reaction mixture was allowed to warm to room temperature, followed by stirring for 30 minutes. The reaction mixture was diluted with chloroform, and then washed with water. The thus-obtained organic layer was dried over anhydrous magnesium sulfate, and then concentrated under reduced pressure. The thus-obtained crude aldehyde was employed in the next reaction without purification thereof.

The crude aldehyde was dissolved in dichloromethane (40.0 ml), and carbon tetrabromide (2.08 g, 6.27 mmol) and triphenylphosphine (3.28 g, 12.5 mmol) were added to the resultant solution at 0° C., followed by stirring at room temperature for one hour. After triethylamine (2.60 ml, 18.7 mmol) was added to the resultant reaction mixture, the resultant mixture was diluted with chloroform, and the resultant organic layer was washed with water. The organic layer was dried over anhydrous magnesium sulfate, and then concentrated under reduced pressure. The resultant residue was purified by means of silica gel column chromatography (silica gel 100 ml, hexane:ethyl acetate=3:1), to thereby yield a crude dibromoethene (1.42 g).

The crude dibromoethene (1.42 g, 2.89 mmol) was dissolved in dry tetrahydrofuran (20.0 ml), and a solution of 2.2-M methyllithium in ether (4.49 ml, 9.88 mmol) was added to the resultant solution in an argon atmosphere at −10° C., followed by stirring at the same temperature for five minutes. Chlorotriethylsilane (0.95 ml, 5.66 mmol) was added to the resultant mixture, and the mixture was further stirred for 30 minutes. After a saturated aqueous solution of ammonium chloride was added to the resultant reaction mixture, the resultant mixture was stirred, and then subjected to extraction with ethyl acetate. The resultant organic layer was dried over anhydrous magnesium sulfate, and then concentrated under reduced pressure, to thereby yield a crude alkyne.

The crude alkyne was dissolved in acetic acid (80.0 ml), and water (20.0 ml) was added to the resultant solution, followed by stirring at room temperature overnight. The resultant reaction mixture was concentrated under reduced pressure, and the resultant residue was co-boiled with toluene. The resultant residue was purified by means of silica gel column chromatography (silica gel 50 ml, hexane:ethyl acetate=3:1), to thereby yield compound 16 (0.70 g, 2.13 mmol, 64.4%).

$^1$H-NMR (CDCl$_3$) δ6.00(1H, d, H-1, J=3.50), 4.60(1H, d, H-2, J=4.00), 4.58(1H, d, H-3, J=5.00), 3.96-3.91(3H, m, H-5 and 3-OH), 2.50(1H, t, 5-OH), 1.64, 1.33(each 3H, s, acetonide), 0.97(9H, t, Et, J=8.00), 0.59(6H, q, Et, J=8.00).

(2) Synthesis of 5-O-t-butyldiphenylsilyl-1,2-O-isopropylidene-4-C-triethylsilylethynyl-α-D-xylopentofuranose (compound 17)

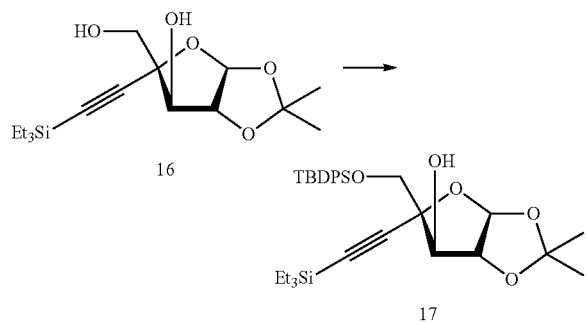

Compound 16 (0.70 g, 2.13 mmol) was dissolved in dimethylformamide (3.50 ml), and t-butylchlorodiphenylsilane (0.66 ml, 2.54 mmol) and imidazole (0.35 g, 5.14 mmol) were added to the resultant solution, followed by stirring overnight. After methanol was added to the resultant reaction mixture, and the resultant mixture was concentrated under reduced pressure, the thus-obtained residue was dissolved in ethyl acetate. The resultant organic layer was washed with water, and then dried over anhydrous magnesium sulfate, and concentrated under reduced pressure. The resultant residue was purified by means of silica gel column chromatography (silica gel 100 ml, hexane:ethyl acetate=5:1), to thereby yield compound 17 (1.10 g, 1.94 mmol, 91.1%).

$^1$H-NMR (CDCl$_3$) δ7.72-7.36(10H, s, aromatic), 6.02(1H, d, H-1, J=3.50), 4.66(1H, d, H-3. J=5.50), 4.63(1H, d, H-1, J=4.00), 4.05(1H, d, H-5a, J=10.5), 3.99(1H, d, 3-OH, J=5.50), 3.93(1H, d, H-5'b, J=10.5), 1.65, 1.35(each 3H, s, acetonide), 1.06(9H, s, t-Bu), 0.93(9H, t, Et, J=8.00), 0.56 (6H, q, Et, J=8.00).

(3) Synthesis of 5-O-t-butyldiphenylsilyl-3-deoxy-1,2-O-isopropylidene-4-C-triethylsilylethynyl-α-D-xylo-pentofuranose (compound 18)

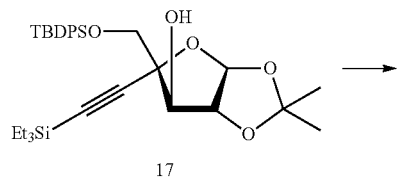

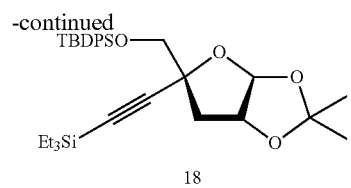

Compound 17 (1.10 g, 1.94 mmol) was dissolved in acetonitrile (20.0 ml), and phenyl chlorothionoformate (0.40 ml, 2.89 mmol) and 4-dimethylaminopyridine (0.71 g, 5.81 mmol) were added to the resultant solution, followed by stirring at room temperature for three hours. The resultant reaction mixture was diluted with ethyl acetate, and then the resultant organic layer was washed with 0.1-N hydrochloric acid and a saturated aqueous solution of sodium bicarbonate. The resultant organic layer was dried over anhydrous magnesium sulfate, and concentrated under reduced pressure. The thus-obtained crude thiocarbonate was employed in the next reaction without purification thereof.

The crude thiocarbonate was co-boiled with toluene three times, and then dissolved in toluene (30.0 ml), followed by degassing under reduced pressure. Tributyltin hydride (2.61 ml, 9.70 mmol) and a small amount of azobis(isobutyronitrile) were added to the resultant solution in an argon atmosphere at 80° C., and the resultant mixture was stirred under the same conditions for one hour. The resultant reaction mixture was concentrated under reduced pressure, and then the thus-obtained residue was purified by means of silica gel column chromatography (silica gel 100 ml, hexane:ethyl acetate=10:1), to thereby yield compound 18 (1.07 g, 1.94 mmol, quant.).

$^1$H-NMR (CDCl$_3$) δ7.69-7.38(10H, m, aromatic), 5.90(1H, d, H-1, J=4.00), 4.85(1H, t, H-2, J=5.00), 3.82(1H, d, H-5a, J=11.0), 3.58(1H, d, H-5b, J=10.5), 2.64(1H, dd, H-3a, J=6.00, 14.0); 2.40(1H, d, H-3b, J=14.0), 1.68, 1.36 (each 3H, s, acetonide), 1.04(9H, s, t-Bu) 0.92(9H, t, Et, J=8.00), 0.54(6H, q, Et, J=8.00).

(4) Synthesis of 1,2-di-O-acetyl-5-O-t-butyldiphenylsilyl-3-deoxy-4-C-triethylsilylethynyl-D-xylopentofuranose (compound 19)

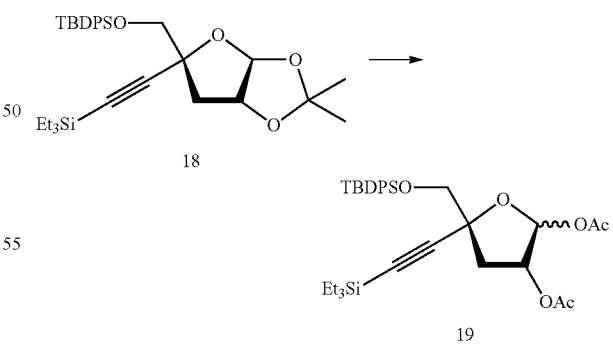

Compound 18 (1.07 g, 1.94 mmol) was dissolved in 80% acetic acid (100 ml), and trifluoroacetic acid (10.0 ml) was added to the resultant solution, followed by stirring at 40° C. for three hours. The resultant reaction mixture was concentrated under reduced pressure, and then the thus-obtained residue was co-boiled with toluene. The resultant residue was purified by means of silica gel column chromatography (silica gel 100 ml, hexane:ethyl acetate=4:1). The resultant residue was dissolved in pyridine (20.0 ml), and acetic anhydride (0.49 ml) was added to the resultant solution, followed by stirring at room temperature overnight. The resultant reaction mixture was concentrated under reduced pressure, and then the thus-obtained residue was co-boiled with toluene. The resultant residue was purified by means of silica gel column chromatography (silica gel 100 ml, hexane:ethyl acetate=5:1), to thereby yield compound 19 (0.75 g, 1.26 mmol, 64.9%).

$^1$H-NMR (CDCl$_3$) δ7.71-7.37(10H, m, aromatic), 6.44(0.3H, d, H-1-alpha, J=4.50), 6.30(0.7H, s, H-1-beta), 5.36(0.3H, m, H-2-alpha), 5.19(0.7H, d, H-2-beta, J=5.50), 3.77, 3.74(each 0.7H, d, H-5-beta, J=10.0), 3.76, 3.62(each 0.3H, d, H-5-alpha, J=11.0), 2.86(0.3H, dd, H-3a-alpha, J=8.50, 12.5), 2.72(0.7H, dd, H-3a-beta, J=5.50, 14.0), 2.39 (0.3H, dd, H-3b-alpha, J=10.0, 12.5), 2.33(0.7H, d, H-3b-beta, J=14.0), 2.11, 2.08(each 0.9H, s, acetyl-alpha), 2.10, 1.80(each 2.1H, s, acetyl-beta), 1.074(6.3H, s, t-Bu-beta), 1.067(2.7H, s, t-Bu-alpha), 0.97(6.3H, t, Et-beta, J=8.00), 0.94(2.7H, t, Et-alpha, J=8.00), 0.58(4.2H, q, Et-beta, J=8.00), 0.54(1.8H, q, Et-alpha, J=8.00).

(5) Synthesis of 9-(2-O-acetyl-5-O-t-butyldiphenyl-silyl-3-deoxy-4-C-triethylsilylethynyl-β-D-xylo-pentofuranosyl)-2,6-diaminopurine (compound 20)

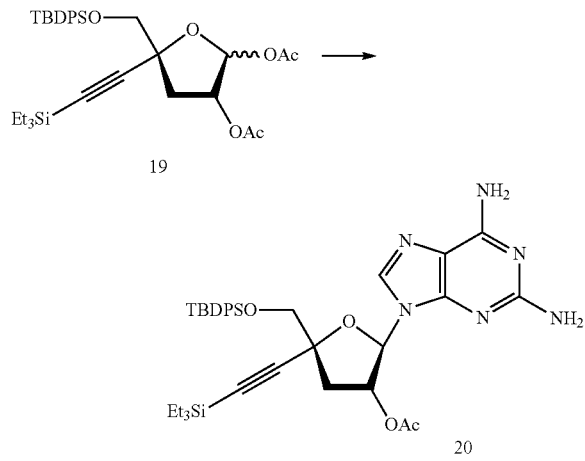

2,6-Diaminopurine (1.21 g, 8.06 mmol) was suspended in acetonitrile (24.0 ml), and N,O-bis(trimethylsilyl)acetamide (11.9 ml, 48.1 mmol) was added to the resultant suspension, followed by stirring at 80° C. for three hours. The resultant solution was concentrated under reduced pressure, and then the thus-obtained residue was co-boiled with 1,2-dichloroethane three times. To the resultant residue, a solution of compound 19 (2.39 g, 4.02 mmol) in 1,2-dichloroethane (24.0 ml), and trimethylsilyl trifluoromethanesulfonate (3.05 ml, 16.9 mmol) were added, and the resultant mixture was stirred in an argon atmosphere at 50° C. for five hours and at 80° C. for 10 hours. After a saturated aqueous solution of sodium bicarbonate was added to the resultant mixture, and then the mixture was stirred, the resultant solution was filtered through celite. The resultant organic layer was dried over anhydrous magnesium sulfate, and then concentrated under reduced pressure. The thus-obtained residue was purified by means of silica gel column chromatography (silica gel 300 ml, chloroform:methanol=20:1). The thus-purified residue was crystallized from hexane and ethyl acetate, to thereby yield compound 20 (1.60 g, 2.34 mmol, 58.2%).

$^1$H-NMR (CDCl$_3$) δ7.67-7.33(10H, m, aromatic), 6.13(1H, d, H-1', J=3.50), 5.77(1H, md, H-2'), 5.28(2H, bs, NH$_2$), 4.49(2H, bs, NH$_2$), 3.67(1H, d, H-5'a, J=10.5), 3.79 (1H, d, H-5'b, J=11.0), 3.18(1H, dd, H-3'a, J=7.50, 14.0), 2.37(1H, dd, H-3'b, J=3.00, 14.0), 1.06(9H, s, t-Bu), 0.99(9H, t. Et, J=8.00), 0.61(6H, q, Et, J=8.00).

(6) Synthesis of 5'-O-t-butyldimethylsilyl-3'-deoxy-4'-C-triethylsilylethynyl-2-fluoroadenosine (compound 21)

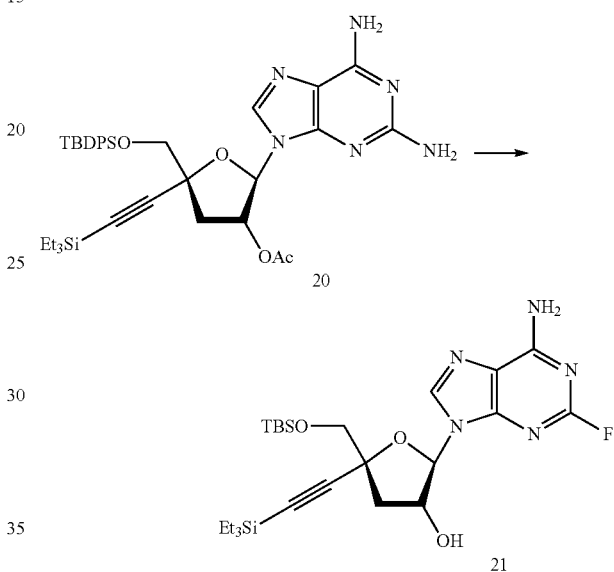

Compound 20 (100 mg, 0.146 mmol) was dissolved in pyridine (3.00 ml), and hydrogen fluoride-pyridine (7.00 ml) and t-butyl nitrite (160 μl, 1.34 mmol) were added to the resultant solution at −15° C., followed by stirring at the same temperature for 30 minutes. After water was added to the resultant reaction mixture, the resultant mixture was subjected to extraction with ethyl acetate. The resultant organic layer was washed with a saturated aqueous solution of sodium bicarbonate, and then dried over anhydrous magnesium sulfate and concentrated under reduced pressure. The thus-obtained residue was purified by means of silica gel column chromatography (silica gel 300 ml, chloroform:methanol=100:1 to 20:1). The resultant residue (48.9 mg) was dissolved in dichloromethane (1.30 ml), and t-butyldimethylsilyl trifluoromethanesulfonate (36.0 μl, 0.157 mmol) and collidine (44.1 μl, 0.0331 mmol) were added to the resultant solution at 0° C., followed by stirring at the same temperature for 50 minutes. Water was added to the resultant reaction mixture, and the resultant mixture was subjected to extraction with chloroform. The resultant organic layer was washed with 0.01-N hydrochloric acid and a saturated aqueous solution of sodium bicarbonate, and then dried over anhydrous magnesium sulfate and concentrated under reduced pressure. The resultant residue was dissolved in dioxane (3.00 ml), and 28% aqueous ammonia (0.30 ml) was added to the resultant solution, followed by stirring at room temperature for 30 minutes. The resultant reaction mixture was concentrated under reduced pressure, and then the thus-obtained residue was dissolved in methanol (1.20 ml), and 28% aqueous ammonia (0.80 ml) was added to the resultant solution, followed by stirring at room temperature for two hours. The resultant reaction mixture was concentrated under reduced pressure, and the thus-precipitated crystals were recovered through filtration, to thereby yield compound 21 (34.0 mg, 0.0652 mmol, 44.7%).

$^1$H-NMR (CDCl$_3$) δ8.04(1H, s, H-8), 5.99(1H, d, H-1', J=4.00), 5.80(2H, bs, NH$_2$), 4.73(1H, m, H-2'), 4.23(1H, d, 2'-OH, J=5.00), 3.88(1H, d, H-5'a, J=11.0), 3.70(1H, d, H-5'b, J=11.0), 2.82(1H, dd, H-3'a, J=7.50, 13.0), 2.42(1H, dd, H-3'b, J=6.50, 13.0), 1.01(9H, t, Et, J=8.00), 0.80(9H, s, t-Bu), 0.64(6H, q, Et, J=8.00), 0.039, −0.013(each 3H, s, Me).

(7) Synthesis of 5'-O-t-butyldimethylsilyl-2',3'-dideoxy-4'-C-triethylsilylethynyl-2-fluoroadenosine (compound 22)

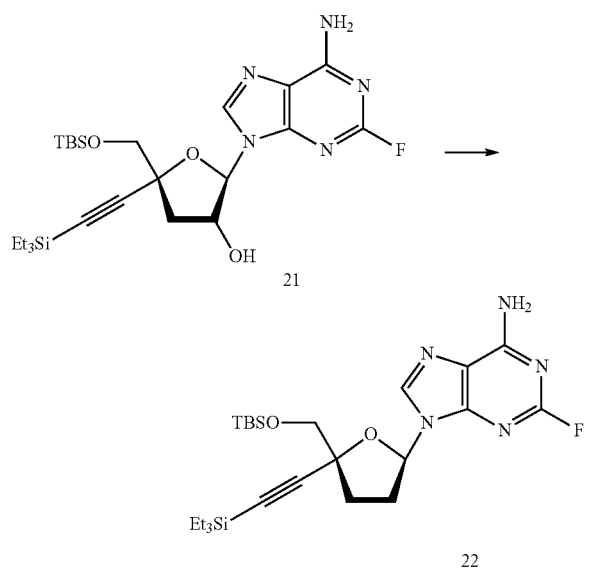

Compound 21 (32.0 mg, 0.061 mmol) was co-boiled with acetonitrile three times, and then dissolved in acetonitrile (1.00 ml). To the resultant solution, phenyl chlorothionoformate (12.7 μl, 0.092 mmol) and 4-dimethylaminopyridine (22.5 mg, 0.180 mmol) were added, and the resultant mixture was stirred at room temperature for one hour. The resultant reaction mixture was diluted with ethyl acetate, and then the thus-obtained organic layer was washed with 0.01-N hydrochloric acid and a saturated aqueous solution of sodium bicarbonate, and dried over anhydrous magnesium sulfate. The resultant organic layer was concentrated under reduced pressure, and the thus-obtained crude thiocarbonate was employed in the next reaction without purification thereof.

The crude thiocarbonate was co-boiled with toluene three times, and then dissolved in toluene (1.00 ml), followed by degassing under reduced pressure. To the resultant solution, tris(trimethylsilyl)silane (94.6 μl, 0.306 mmol) and a small amount of azobis(isobutyronitrile) were added in an argon atmosphere at 80° C., and the resultant mixture was stirred under the same conditions for one hour. The resultant reaction mixture was concentrated under reduced pressure, and then the thus-obtained residue was purified by means of silica gel column chromatography (silica gel 10 ml, chloroform:methanol=200:1 to 100:1), to thereby yield compound 22 (26.1 mg, 0.0516 mmol, 84.6%).

$^1$H-NMR (CDCl$_3$) δ8.24(1H, s, H-8), 6.36(1H, dd, H-1', J=2.50, 7.00), 5.91(2H, bs, NH$_2$), 4.04(1H, d, H-5'a, J=11.0), 3.81(1H, d, H-5'b, J=11.0), 2.83(1H, m, H-2'a), 2.54(1H, m, H-3'a), 2.37(1H, m, H-2'b), 2.11(1H, m, H-3'b), 1.00(9H, t, Et, J=8.00), 0.93(9H, s, t-Bu), 0.62(6H, q, Et, J=8.00), 0.13 (6H, s, Me).

(8) Synthesis of 2',3'-dideoxy-4'-C-ethynyl-2-fluoroadenosine (compound 23)

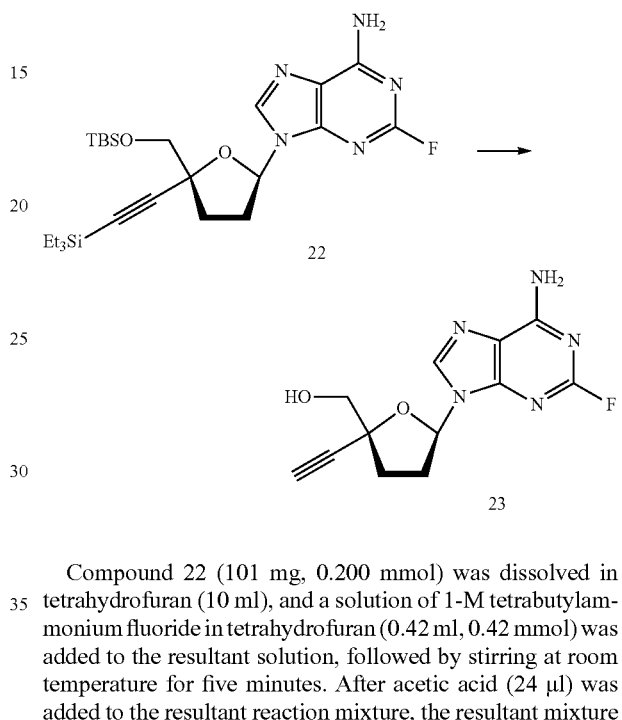

Compound 22 (101 mg, 0.200 mmol) was dissolved in tetrahydrofuran (10 ml), and a solution of 1-M tetrabutylammonium fluoride in tetrahydrofuran (0.42 ml, 0.42 mmol) was added to the resultant solution, followed by stirring at room temperature for five minutes. After acetic acid (24 μl) was added to the resultant reaction mixture, the resultant mixture was concentrated under reduced pressure. The thus-obtained residue was purified by means of silica gel column chromatography (silica gel 15 ml, chloroform:methanol=40:1 to 20:1), to thereby yield compound 23 (53.0 mg, 0.191 mmol, 95.7%).

$^1$H-NMR (MeOD) δ8.23(1H, s, H-8), 6.22(1H, dd, H-1', J=4.00, 7.00), 3.77(1H, d, H-5'a, J=12.5), 3.61(1H, d, H-5'b, J=12.0), 2.94(1H, s, ethynyl), 2.66(1H, m, H-2'a), 2.54(1H, m, H-3'a), 2.42(1H, m, H-2'b), 2.11(1H, m, H-3'b).

Synthesis Example 8

Synthesis of 2',3'-dideoxy-4'-C-ethynyl-2-fluoroadenosine 5'-H-phosphonate (compound 24)

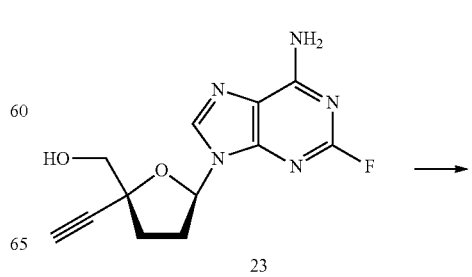

-continued

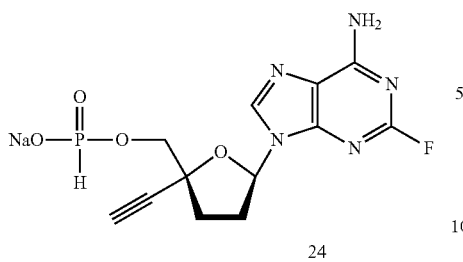

24

Compound 23 (20.0 mg, 0.07 mmol) was dissolved in pyridine (1 ml), and phosphonic acid (11.8 mg, 0.144 mmol) and dicyclohexyl carbodiimide (44.7 mg, 0.216 mmol) were added to the resultant solution, followed by stirring at room temperature for five hours. The resultant reaction mixture was concentrated under reduced pressure, and the thus-obtained residue was purified by means of ODS column chromatography (ODS 10 ml, 0 to 1% acetonitrile). The resultant residue was applied to a Dowex 50Wx8 column (Na type) and eluted. The eluate was concentrated, and the resultant residue was treated with methanol and ether, to thereby yield a powdery compound (compound 24; 4.7 mg, 13 μmol, 18.6%).

$^1$H-NMR (MeOD) δ8.37(1H, s, H-8), 6.77(1H, d, H—P, J=625), 6.32(1H, dd, H-1', J=4.00, 6.50), 4.09(1H, m, H-5'), 2.71(2H, m, H-2'a, H-3'a), 2.52(1H, m, H-2'b), 2.29(1H, m, H-3'b).

$^{31}$P-NMR (MeOD) δ4.52.

Drug Preparation Example 1

Tablets

| | |
|---|---|
| Compound of the present invention | 30.0 mg |
| Cellulose micropowder | 25.0 mg |
| Lactose | 39.5 mg |
| Starch | 40.0 mg |
| Talc | 5.0 mg |
| Magnesium stearate | 0.5 mg |

Tablets are prepared from the above composition through a customary method.

Drug Preparation Example 2

Capsules

| | |
|---|---|
| Compound of the present invention | 30.0 mg |
| Lactose | 40.0 mg |
| Starch | 15.0 mg |
| Talc | 5.0 mg |

Capsular drugs are prepared from the above composition through a customary method.

Drug Preparation Example 3

Injections

| | |
|---|---|
| Compound of the present invention | 30.0 mg |
| Glucose | 100.0 mg |

Injections are prepared by dissolving the above composition in purified water for preparing injections.

Test Examples will next be described. Employed in tests were the following five compounds of the present invention and four known compounds.

Invention Compounds:
  Compound 4: 2'-deoxy-4'-C-ethynyl-2-fluoroadenosine;
  Compound 8: 4'-C-cyano-2'-deoxy-2-fluoroadenosine;
  Compound 9: 2-chloro-2'-deoxy-4'-C-ethynyladenosine;
  Compound 10: 2'-deoxy-4'-C-ethynyl-2-fluoroadenosine 5'-H-phosphonate; and
  Compound 13: 2',3'-didehydro-2',3'-dideoxy-4'-C-ethynyl-2-fluoroadenosine.

Known Compounds:
  AZT: Azidothymidine;
  EdAdo: 2'-deoxy-4'-C-ethynyladenosine;
  EdDAP: 9-(4-C-ethynyl-2-deoxy-ribopentofuranosyl)-2,6-diaminopurine; and
  ddAdo: 2',3'-dideoxyadenosine.

Test Example 1

<Test Methods> Anti-Human-Immunodeficiency-Virus (HIV) Activity
1) MTT Method Using MT-4 Cells
  1. A test agent (100 μl) is diluted on a 96-well microplate. MT-4 cells infected with HIV-1 (IIIb strain; 100 TCID$_{50}$) and non-infected MT-4 cells are added to the microplate such that the number of cells in each well becomes 10,000. The cells are cultured at 37° C. for five days.
  2. MTT (20 μl, 7.5 mg/ml) is added to each well, and the cells are further cultured for 2-3 hours.
  3. The cultured medium (120 μl) is sampled, and MTT terminating solution (isopropanol containing 4% Triton X-100 and 0.04N HCl) is added to the sample. The mixture is stirred to dissolve formed formazan. The absorbance at 540 nm of the solution is measured. Since the absorbance is proportional to the number of viable cells, the test agent concentration at which a half value of the absorbance is measured in a test using infected MT-4 cells represents EC$_{50}$, whereas the test agent concentration at which a half value of the absorbance is measured in a test using non-infected MT-4 cells represents CC$_{50}$.
2) MAGI Assay Using HeLa CD4/LTR-beta-Gal Cells
  1. HeLa CD4/LTR-beta-Gal cells are added to 96 wells such that the number of cells in each well is 10,000. After 12-24 hours, the culture medium is removed, and a diluted test agent (100 μl) is added.
  2. A variety of HIV strains (wild strain: WT, drug-resistant strain: MDR and M184V; each being equivalent to 50 TCID$_{50}$) are added, and the cells are further cultured for 48 hours.
  3. The cells are fixed for five minutes using PBS supplemented with 1% formaldehyde and 0.2% glutaraldehyde.

4. After the fixed cells are washed with PBS three times, the cells are stained with 0.4 mg/ml X-Gal for one hour, and the number of blue-stained cells of each well is counted under a transmission stereoscopic microscope. The test agent concentration at which blue-stained cells decrease to 50% in number represents $EC_{50}$.

<Results> Anti-human-immunodeficiency Virus (HIV) Activity and Cytotoxicity

1) MTT Method Using MT-4 Cells

TABLE 1

| | MT-4 cells | | |
|---|---|---|---|
| Drugs | Anti-HIV-1 activity ($EC_{50}$, μM) | Cytotoxicity ($CC_{50}$, μM) | Selectivity Index ($CC_{50}/EC_{50}$) |
| Compound 4 | 0.000068 | 7.5 | 110000 |
| EdDAP | 0.00034 | 0.9 | 2600 |
| EdAdo | 0.0098 | 16 | 1630 |
| AZT | 0.0032 | 29.4 | 9190 |

2) MAGI Assay Using HeLa CD4/LTR-beta-Gal Cells

TABLE 2

| | HeLa CD4/LTR-beta-Gal cells | | |
|---|---|---|---|
| Drugs | Anti-HIV-1$_{wild}$ activity ($EC_{50}$, μM) | Anti-HIV-1$_{MDR}$ activity ($EC_{50}$, μM) | Anti-HIV-1$_{M184V}$ activity ($EC_{50}$, μM) |
| Compound 4 | 0.00020 | 0.0001448 | 0.003107 |
| Compound 8 | 0.12 | 0.95 | 4.8 |
| Compound 9 | 0.0019 | 0.0084 | 0.01 |
| Compound 10 | 0.0034 | 0.003 | 0.062 |
| Compound 13 | 0.80 | 0.15 | 1.8 |
| EdAdo | 0.008 | 0.0062 | 0.047 |
| AZT | 0.022 | 15.3 | 0.01 |

Test Example 2

<Test Methods> Stability of Compound 4 Against Adenosine Deaminase

Calf-intestine-derived adenosine deaminase (0.01 unit) was added to 0.5 ml of 0.5-mM compound 4 (50 mM Tris-HCl buffered solution (pH 7.5)), and the mixture was incubated at 25° C.

A 5-μl aliquot of the reaction mixture was removed every 15 minutes, followed by analysis by means of HPLC (high performance liquid chromatography). The peak area of a test drug at reaction time 0 was taken as 100%, and the curve was monitored over time. The HPLC analysis was performed under the following conditions.

Column: YMC-Pack ODS-A (250×6.0 mm)

Eluent: 15% MeCN-50 mM TEAA

Flow rate: 1 mL/min.

Temperature: 30° C.

Detection: 260 nm

<Results>

As shown in FIG. 1, 2'-deoxy-4'-C-ethynyl-2-fluoroadenosine, which is Compound 4 of the present invention, was not at all deaminated, as contrasted to the case where conventional 2'-deoxy-4'-C-ethynyladenosine (EdAdo) was deaminated, proving that the compound of the present invention has resistance to adenosine deaminase.

Test Example 3

<Test Methods> Stability of Compound 4 Under Acidic Conditions

Compound 4 (2.9 mg) or 2',3'-dideoxyadenosine (ddAdo: 2.4 mg) was dissolved in 10 ml of a 37° C. test solution (which had been prepared by adding 2.0 g of sodium chloride and 7.0 ml of hydrochloric acid into water to make a solution of 1,000 ml), followed by incubation at the same temperature (37° C.).

A 100-μl aliquot of the reaction mixture was removed therefrom and neutralized with aqueous 0.1-N sodium hydroxide solution, followed by analysis of 5 μl by means of HPLC. The HPLC analysis conditions are the same as those employed in Test Example 2.

<Results>

Figure 2:
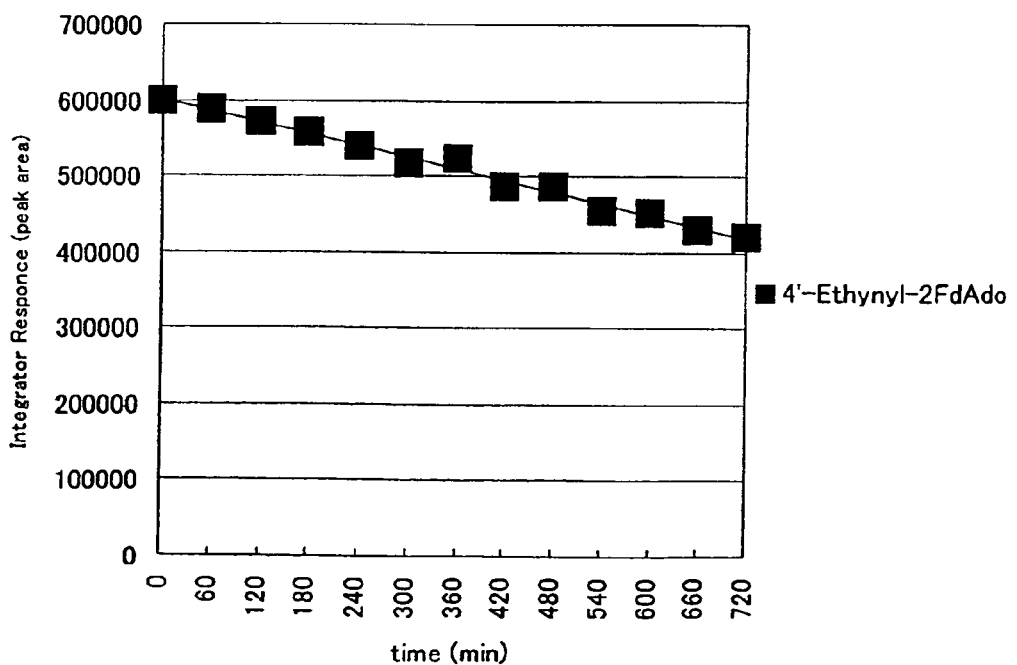
FIG. 2 shows stability of 2'-deoxy-4'-C-ethynyl-2-fluoroadenosine (a compound of the present invention) under acidic conditions.
Figure 3:
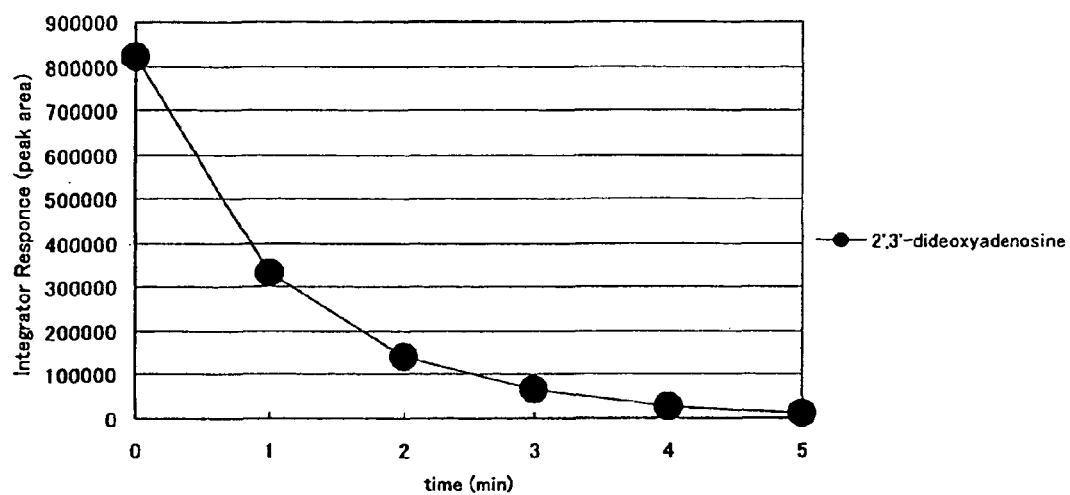
FIG. 3 shows stability of 2',3'-dideoxyadenosine (ddAdo; a known compound) under acidic conditions.

About 98% of ddAdo, which is a conventional compound, is degraded in about five minutes under the above conditions (see FIG. 3), whereas 2'-deoxy-4'-C-ethynyl-2-fluoroadenosine, which is Compound 4 of the present invention, was degraded very slowly, proving that the compound of the present invention is relatively stable under acidic conditions (see FIG. 2).

Test Example 4

<Test methods> In vivo Acute Toxicity Test of Compound 4

Groups of ICR mice (6 weeks of age, male), each group consisting of 8 mice, were given a test drug (Compound 4; dissolved or suspended in saline) via oral route or intravenous injection in amounts up to 100 mg/kg. The occurrence of death and body weight of each mouse were monitored for seven days.

<Results>

Figure 4:
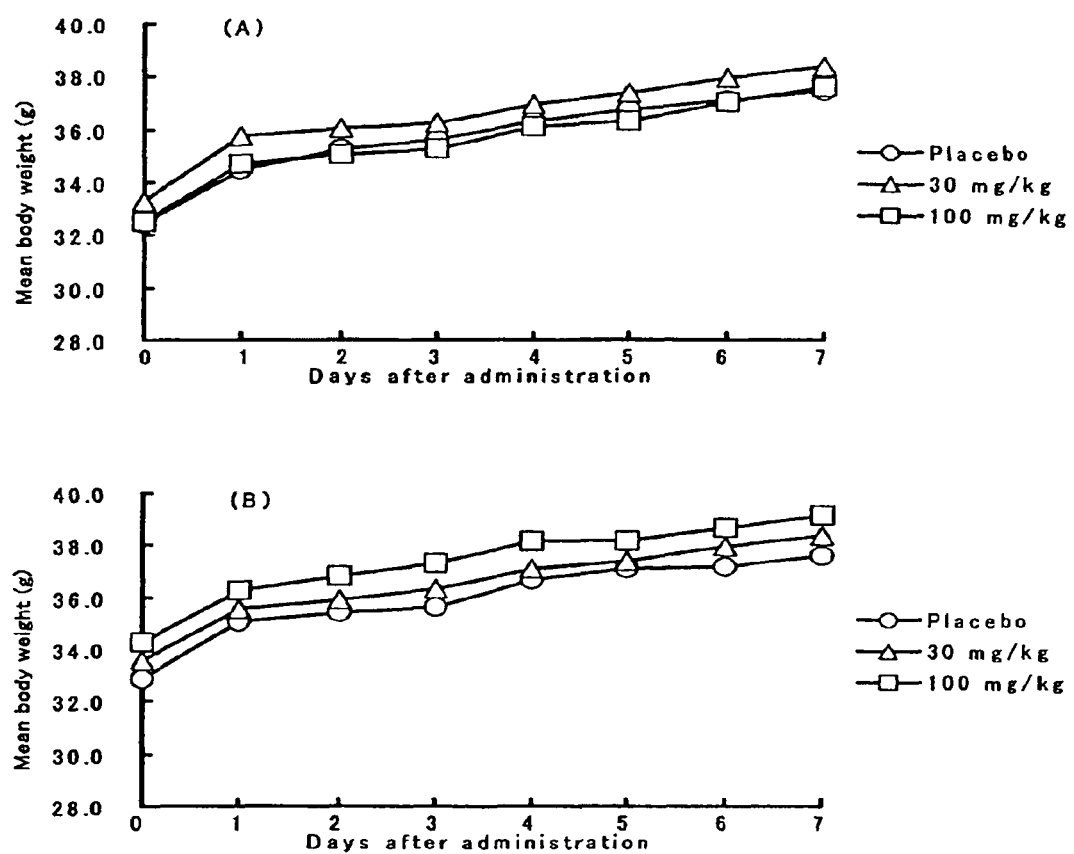
FIG. 4 shows changes in body weight of mice, as measured after administration of 2'-deoxy-4'-C-ethynyl-2-fluoroadenosine (a compound of the present invention).

All the mice to which Compound 4 was administered up to 100 mg/kg in a single dose survived regardless of the administration route of oral or intravenous (Table 3). Also, as shown in FIG. 4, weight loss and pathological symptoms such as diarrhea were not observed. Thus, it has now been confirmed that 2'-deoxy-4'-C-ethynyl-2-fluoroadenosine (Compound 4) of the present invention does not exhibit acute toxicity in mice.

TABLE 3

| | Survivors/Total | |
|---|---|---|
| Dose (mg/kg) | Oral | Intravenous |
| Placebo | 8/8 | 8/8 |
| 1 | 8/8 | 8/8 |
| 3 | 8/8 | 8/8 |
| 10 | 8/8 | 8/8 |
| 30 | 8/8 | 8/8 |
| 100 | 8/8 | 8/8 |

What is claimed is:

1. A method for producing a 4'-C-substituted-2-haloadenosine compound represented by formula [I]:

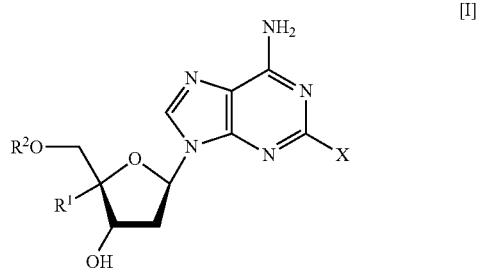

wherein X represents a fluorine or chlorine atom, $R^1$ represents an ethynyl group or a cyano group, and $R^2$ represents hydrogen, the method comprising:

a first step of protecting hydroxyl groups at the 3'- and 5'-positions of a compound represented by formula [IV]:

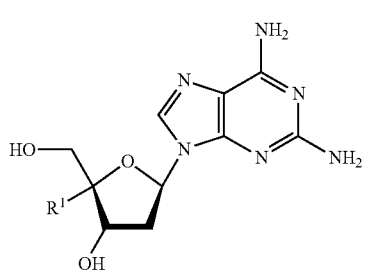

[IV]

wherein $R^1$ represents an ethynyl group or a cyano group, to provide a compound represented by formula [V]:

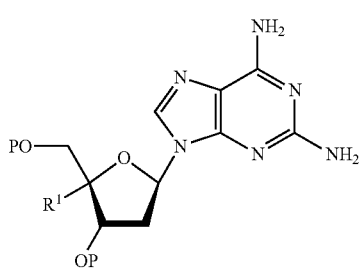

[V]

wherein P represents a protective group, and $R^1$ represents an ethynyl group or a cyano group;

a second step of treating the amino group at the 2-position of the compound represented by formula [V] with a nitrite derivative and a halogen reagent to introduce a halogen atom at the 2-position thereof, to provide a compound represented by formula [VI]:

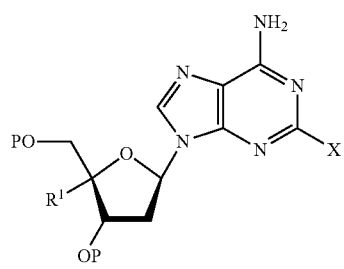

[VI]

wherein P represents a protective group, X represents a fluorine or chlorine atom, and $R^1$ represents an ethynyl group or a cyano group; and a third step of removing the protective groups of the resultant compound to provide a compound represented by formula [I], wherein the nitrite derivative and the halogen reagent in the second step are selected from the group consisting of sodium nitrite and tetrafluoroboric acid, a nitrous acid ester and hydrogen fluoride-pyridine, a combination of antimony trichloride and t-butyl nitrite in an organic solvent and a combination of acetyl chloride and benzyltriethylammonium nitrite in an organic solvent.

2. The method according to claim 1, wherein the protective groups represented by P are ether type protective groups, acyl type protective groups, silyl type protective groups, or acetal type protective groups.

* * * * *

UNITED STATES PATENT AND TRADEMARK OFFICE
CERTIFICATE OF CORRECTION

PATENT NO. : 8,039,614 B2
APPLICATION NO. : 12/453732
DATED : October 18, 2011
INVENTOR(S) : Satoru Kohgo It is certified that error appears in the above-identified patent and that said Letters Patent is hereby corrected as shown below:

On the Title Page
In Section (12), "Kohgo et al." should read --Kohgo--.

In Section (75), Inventors: "Satoru Kohgo, Kashima-gun (JP); Hiroshi Ohrui, Sendai (JP); Eiichi Kodama, Kyoto (JP); Masao Matsuoka, Otsu (JP); Hiroaki Mitsuya, Kumamoto (JP)" should read --Satoru Kohgo, Kashima-gun (JP)--.

Signed and Sealed this
Seventh Day of February, 2012

David J. Kappos
*Director of the United States Patent and Trademark Office*